United States Patent
Zajac-Kaye et al.

(10) Patent No.: US 10,835,524 B2
(45) Date of Patent: Nov. 17, 2020

(54) COMPOSITIONS FOR THE TREATMENT OF PANCREATIC CANCER AND USES THEREOF

(71) Applicant: University of Florida Research Foundation, Incorporated, Gainesville, FL (US)

(72) Inventors: Maria Zajac-Kaye, Gainesville, FL (US); Rony A. Francois, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 198 days.

(21) Appl. No.: 15/737,545

(22) PCT Filed: Jun. 16, 2016

(86) PCT No.: PCT/US2016/037731
§ 371 (c)(1),
(2) Date: Dec. 18, 2017

(87) PCT Pub. No.: WO2016/209688
PCT Pub. Date: Dec. 29, 2016

(65) Prior Publication Data
US 2018/0177776 A1    Jun. 28, 2018

Related U.S. Application Data

(60) Provisional application No. 62/183,831, filed on Jun. 24, 2015.

(51) Int. Cl.
| | | |
|---|---|---|
| *A61K 31/4709* | (2006.01) | |
| *A61K 31/436* | (2006.01) | |
| *A61K 31/4745* | (2006.01) | |
| *A61K 31/4184* | (2006.01) | |
| *A61P 35/00* | (2006.01) | |
| *A61K 31/4375* | (2006.01) | |

(52) U.S. Cl.
CPC ...... *A61K 31/4709* (2013.01); *A61K 31/4184* (2013.01); *A61K 31/436* (2013.01); *A61K 31/4375* (2013.01); *A61K 31/4745* (2013.01); *A61P 35/00* (2018.01)

(58) Field of Classification Search
CPC .......................... A61K 31/4709; A61P 35/00
USPC .......................................................... 514/311
See application file for complete search history.

(56) References Cited

U.S. PATENT DOCUMENTS

| | | |
|---|---|---|
| 4,992,444 A | 2/1991 | Stevens et al. |
| 5,635,515 A | 6/1997 | Chauffert et al. |
| 6,525,091 B2 | 2/2003 | Robinson et al. |
| 6,984,647 B2 | 1/2006 | Dax et al. |
| 2003/0216426 A1 | 11/2003 | Carson et al. |
| 2005/0038031 A1 | 2/2005 | Dumas et al. |
| 2005/0143588 A1 | 6/2005 | Heaton et al. |
| 2005/0154010 A1 | 7/2005 | Carson et al. |
| 2006/0166925 A1 | 6/2006 | Dolezal et al. |
| 2007/0099976 A1 | 5/2007 | Halperin et al. |
| 2007/0161546 A1 | 7/2007 | King |
| 2008/0045589 A1 | 2/2008 | Kelley |
| 2009/0203636 A1 | 8/2009 | Bondarev |
| 2010/0009934 A1 | 1/2010 | Rickles et al. |
| 2010/0260772 A1 | 10/2010 | Karsenty |
| 2011/0176996 A1 | 7/2011 | ONeill et al. |
| 2011/0224141 A1 | 9/2011 | Thompson et al. |
| 2012/0082659 A1 | 4/2012 | Thompson et al. |
| 2012/0115915 A1 | 5/2012 | Aktas et al. |
| 2012/0260772 A1 | 10/2012 | Karsenty |
| 2013/0183289 A1 | 7/2013 | Gorelik et al. |
| 2016/0067240 A1 | 3/2016 | Zajac-Kaye et al. |

FOREIGN PATENT DOCUMENTS

| | | |
|---|---|---|
| CN | 102125579 A | 7/2011 |
| JP | S57-081460 | 5/1982 |
| WO | WO 1998/30550 | 7/1998 |
| WO | WO 2003/096992 A2 | 11/2003 |
| WO | WO 2006/049941 A2 | 5/2006 |
| WO | WO 2006/125540 A1 | 11/2006 |
| WO | WO 2010/138820 A2 | 12/2010 |
| WO | WO 2011/151423 | 12/2011 |

OTHER PUBLICATIONS

Pai et al., AKT inhibitors in clinical development for the treatment of cancer, 2010, Expert Opin Investig Drugs, 19(11), pp. 1355-1366. (Year: 2010).*
Yang et al., "Pancreatic cancer require autophagy for tumor growth", Genes and Development, vol. 25, pp. 1-13 (Mar. 2011).*
Yao et al., "Everolinnus for Advanced Neuroendocrine Tumors", The New England Journal of Medicine, vol. 364, No. 6, pp. 514-523 (2011).*
PCT/US2016/037731, Oct. 19, 2016, International Search Report and Written Opinion.
PCT/US2014/030143, Oct. 27, 2014, International Search Report and Written Opinion.
PCT/US2014/030143, Sep. 24, 2015 International Preliminary Report on Patentability.
International Preliminary Report on Patentability, dated Sep. 24, 2015, in connection with PCT/U52014/030143.

(Continued)

*Primary Examiner* — Kevin E Weddington
(74) *Attorney, Agent, or Firm* — Wolf, Greenfield & Sacks, P.C.

(57) ABSTRACT

The invention pertains to compositions comprising inhibitors of PI3K, AKT and/or mTOR, one or more 4-quinolinemethanols and a pharmaceutically acceptable excipient. These compositions can contain subtherapeutic amounts of each active ingredient (PI3K, AKT, mTOR, one or more 4-quinolinemethanols and various combinations thereof). The invention also provides a method of treating various forms of cancer, such as breast cancer, prostate cancer, multiple myeloma, hepatocyte carcinoma, brain cancer, lung cancer, non-small cell lung carcinoma, colorectal cancer, melanoma and/or pancreatic cancer.

28 Claims, 38 Drawing Sheets

(56) References Cited

OTHER PUBLICATIONS

International Search Report and Written Opinion, dated Oct. 27, 2014, in connection with PCT/US2014/030143.
International Search Report and Written Opinion, dated Oct. 19, 2016, in connection with PCT/US2016/037731.
[No Author Listed], CID 280274. Compound Summary. Mar. 26, 2006. https://pubchem.ncbi.nlm.nih.gov/compound/280274#section=Top. [last accessed Jul. 17, 2017]. 14 pages.
[No Author Listed], CID 5911417. Compound Summary. Sep. 10, 2005. https://pubchem.ncbi.nlm.nih.gov/compound/5911417#section=Top. [last accessed Jul. 17, 2017]. 15 pages.
[No Author Listed], CID 42501056. Compound Summary. May 30, 2009.
Aarhus et al., Microarray analysis reveals down-regulation of the tumour suppressor gene WWOX and up-regulation of the oncogene TYMS in intracranial sporadic meningiomas, J Neuro-Oncology, 2008, vol. 88, No. 3, pp. 251-259.
Barlesi et al., Pemetrexed and cisplatin as first-line chemotherapy for advanced non-small-cell lung cancer (NSCLC) with asymptomatic inoperable brain metastases: a multicenter phase II trial (GFPC 07-01 ),Annals of Oncology, 2011, vol. 22, pp. 2466-2470.
Barrows et al., A Screen of FDA-Approved Drugs for Inhibitors of Zika Virus Infection. Cell Host Microbe. Aug. 10, 2016;20(2):259-70. doi: 10.1016/j.chom.2016.07.004. Epub Jul. 28, 2016.
Bermudez et al., Mefloquine and Its Enantiomers Are Active against *Mycobacterium tuberculosis* In Vitro and in Macrophages. Tuberc Res Treat. 2014;2014:530815. doi: 10.1155/2014/530815. Epub Dec. 11, 2014.
Brickelmaier et al., Identification and characterization of mefloquine efficacy against JC virus in vitro. Antimicrob Agents Chemother. May 2009;53(5):1840-9. doi: 10.1128/AAC.01614-08. Epub Mar. 2, 2009.
Brozell et al., Evaluation of DOCK 6 as a pose generation and database enrichment tool, Journal of Computer-Aided Molecular Design, 2012, vol. 26, pp. 749-773.
Cardinale et al., Protein-protein interface-binding peptides inhibit the cancer therapy target human thymidylate synthase, Proceedings of the National Academy of Sciences of the United States of America, Aug. 23, 2011, vol. 108, No. 34, pp. E542-549.
Carreras et al., The catalytic mechanism and structure of thymidylate synthase, Annual Review of Biochemistry, 1995, vol. 64, pp. 721-762.
Ceppi et al., Squamous Cell Carcinoma of the Lung Compared With Other Histotypes Shows Higher Messenger RNA and Protein Levels for Thymidylate Synthase, Cancer, 2006, 107, No. 7, pp. 1589-1596.
Ceppi et al., Thymidylate Synthase Expression in Gastroenteropancreatic and Pulmonary Neuroendocrine Tumors, Clinical Cancer Research, Feb. 15, 2008, vol. 14, No. 4, pp. 1059-1064.
Chang et al., PI3K/Akt/mTOR pathway inhibitors enhance radiosensitivity in radioresistant prostate cancer cells through inducing apoptosis, reducing autophagy, suppressing NHEJ and HR repair pathways. Cell Death Dis. Oct. 2, 2014;5:e1437. doi:10.1038/cddis.2014.415.
Chavchich et al., Role of pfmdr1 amplification and expression in induction of resistance to artemisinin derivatives in Plasmodium falciparum. Antimicrob Agents Chemother. Jun. 2010;54(6):2455-64. doi: 10.1128/AAC.00947-09. Epub Mar. 29, 2010.
Chu et al., Induction of Thymidylate Synthase Associated with Multidrug Resistance in Human Breast and Colon Cancer Cell Lines, Molecular Pharmacology, 1991, vol. 39, No. 2, pp. 136-143.
Copur et al., Thymidylate Synthase Gene Amplification in Human Colon Cancer Cell Lines Resistant to 5-Fluorouracil, Biochemical Pharmacology, 1995, vol. 49, No. 10, pp. 1419-1426.
Crawford et al., Sigma-2 Receptor Agonists Activate a Novel Apoptotic Pathway and Potentiate Antineoplastic Drugs in Breast Tumor Cell Lines, Cancer Research, 2002, vol. 62, pp. 313-322.
Cruikshank et al., Potent block of Cx36 and Cx50 gap junction channels by mefloquine. Proc Natl Acad Sci U S A. Aug. 17, 2004;101(33):12364-9. Epub Aug. 5, 2004.
Danenberg et al., Thymidylate Synthetase—A Target Enzyme in Cancer Chemotherapy, Biochimica et Biophysica Acta, 1977, vol. 473, pp. 73-92.
Edler et al., Thymidylate Synthase Expression: An Independent Prognostic Factor for Local Recurrence, Distant Metastasis, Disease-free and Overall Survival in Rectal Cancer, Clinical Cancer Research, Apr. 2000, vol. 6, No. 4, pp. 1378-1384.
Galvani et al. Thymidylate synthase inhibitors for non-small cell lung cancer. Expert Opinion on Investigational Drugs, 2011, vol. 20, No. 10, pp. 1343-1356.
Geng et al., Chloroquine-induced autophagic vacuole accumulation and cell death in glioma cells is p53 independent. Neuro Oncol. May 2010;12(5):473-81. doi: 10.1093/neuonc/nop048. Epub Jan. 27, 2010.
Gonçalves et al., Mefloquine-oxazolidine derivatives, derived from mefloquine and arenecarbaldehydes: In vitro activity including against the multidrug-resistant tuberculosis strain T113. Bioorg Med Chem. Jan. 1, 2012;20(1):243-8. doi: 10.1016/j.bmc.2011.11.006. Epub Nov. 12, 2011.
Griffin et al., Structural studies on bioactive compounds. 8. Synthesis, crystal structure, and biological properties of a new series of 2,4-diamino-5-aryl-6-ethylpyrimidine dihydrofolate reductase inhibitors with in vivo activity against a methotrexate-resistant tumor cell line. J Med Chem. Nov. 1989;32(11):2468-74.
Grimaudo et al., Selective induction of apoptosis in multidrug resistant HL60R cells by the thiazolobenzoimidazole derivative 1-(2,6-difluorophenyl)-1H,3H-thiazolo [3,4-a] benzimidazole (TBZ). Eur J Cancer. Oct. 1998;34(11):1756-63.
Grunda et al., Increased expression of thymidylate synthetase (TS), ubiquitin specific protease 10 (USP10) and survivin is associated with poor survival in glioblastoma multiforme (GBM), Journal of Neuro-Oncology, 2006, vol. 80, pp. 261-274.
Houssay et al., The Influence Exerted by Desoxycorticosterone Acetate upon the Production of Adrenal Tumors in Gonadectomized Mice, Cancer Research, 1951, vol. 11, No. 5, pp. 297-300.
Irwin et al., ZINC: A Free Tool to Discover Chemistry for Biology, Journal of Chemical Information and Modeling, 2012, vol. 52, No. 7, pp. 1757-1768.
Iwama et al., Epidural Administration of Droperidol Suppresses Cisplatin-induced Emesis: Preliminary Findings, Surgery Today, 1998, vol. 28, pp. 231-234.
Kim et al., Co-treatment with the anti-malarial drugs mefloquine and primaquine highly sensitizes drug-resistant cancer cells by increasing P-gp inhibition. Biochem Biophys Res Commun. Nov. 22, 2013;441(3):655-60. doi: 10.1016/j.bbrc.2013.10.095. Epub Oct. 26, 2013.
Klebe, Virtual ligand screening: strategies, perspectives and limitations. Drug Discovery Today,. Jul. 2006, vol. 11, Nos. 13-14, pp. 580-594.
Krieger et al., Mefloquine as a potential drug against multidrug-resistant tuberculosis. Eur Respir J. Nov. 2015;46(5):1503-5. doi: 10.1183/13993003.00321-2015. Epub Jul. 23, 2015.
Labianca et al., The role of adjuvant chemotherapy in colon cancer, Surgical Oncology, 2007, vol. 16, Suppl. 1, pp. 893-896.
Li et al., Simultaneous determination of vanadium, niobium and tantalum by highperformance liquid chromatography equipped with on-line enrichment using 2-[2-(5-bromoquinolinylazo)]-5-diethylaminophenol as pre-column derivatization agent, Microchimica Acta, 2007, vol. 158, pp. 95-102.
Liu et al., Mefloquine effectively targets gastric cancer cells through phosphatase-dependent inhibition of PI3K/Akt/mTOR signaling pathway. Biochem Biophys Res Commun. Feb. 5, 2016;470(2):350-5. doi:10.1016/j.bbrc.2016.01.046. Epub Jan. 11, 2016.
Longley et al., 5-fluorouracil: mechanisms of action and clinical strategies. Nature Reviews Cancer, May 2003, vol. 3, No. 5, pp. 330-338.
Ma et al., A phase II trial of a combination of pemetrexed and gemcitabine in patients with metastatic breast cancer: an NCCTG study, Annals of Oncology, 2006, vol. 17, No. 2, pp. 226-231.

(56) References Cited

OTHER PUBLICATIONS

Morgan et al., Targeted therapy for advanced prostate cancer: inhibition of the PI3K/Akt/mTOR pathway. Curr Cancer Drug Targets. Mar. 2009;9(2):237-49.
Mukherjee et al., Docking Validation Resources: Protein Family and Ligand Flexibility Experiments, Journal of Chemical Information and Modeling, 2010, vol. 50, No. 11, pp. 1986-2000.
Pereira et al., Spectrophotometric determination of arsenic in soil samples using 2-(5-bromo-2-pyridylazo)-5-di-ethylaminophenol (Br-PADAP), Ecletica Quimica, 2008, vol. 33, No. 3, pp. 23-28.
Phan et al., Human Thymidylate Synthase Is in the Closed Conformation When Complexed with dUMP and Raltitrexed, an Antifolate Drug, Biochemistry, 2001, vol. 40, pp. 1897-1902.
Rahman et al., Thymidylate synthase as an oncogene: A novel role for an essential DNA synthesis enzyme, Cancer Cell, Apr. 2004, vol. 5, No. 4, pp. 341-351.
Ramaswamy et al., Multiclass cancer diagnosis using tumor gene expression signatures, PNAS. Dec. 18, 2001, vol. 98, No. 26, pp. 15149-15154.
Rodrigues et al., Mefloquine-oxazolidine derivatives: a new class of anticancer agents. Chem Biol Drug Des. Jan. 2014;83(1):126-31. doi:10.1111/cbdd.12210. Epub Oct. 5, 2013.
Sachlos et al., Identification of drugs including a dopamine receptor antagonist that selectively target cancer stem cells. Cell. Jun. 8, 2012;149(6):1284-97. doi: 10.1016/j.cell.2012.03.049. Epub May 24, 2012.
Sharma et al., Inhibition of autophagy and induction of breast cancer cell death by mefloquine, an antimalarial agent. Cancer Lett. Dec. 30, 2012;326(2):143-54. doi:10.1016/j.canlet.2012.07.029. Epub Aug. 1, 2012.
Sharma et al., Screening of potential chemopreventive agents using biochemical markers of carcinogenesis. Cancer Res. Nov. 15, 1994;54(22):5848-55.
Sigmond et al., Induction of resistance to the multitargeted antifolate Pemetrexed (ALIMTA) in WiDr human colon cancer cells is associated with thymidylate synthase overexpression, Biochemical Pharmacology, 2003, vol. 66, No. 3, pp. 431-438.
Skibola et al., Polymorphisms and haplotypes in folate-metabolizing genes and risk of non-Hodgkin lymphoma, Blood, Oct. 1, 2004, vol. 104, pp. 2155-2162.
Spielmann et al., Activity of Pemetrexed (ALIMTA®, Multitargeted Antifolate, L Y231514) in Metastatic Breast Cancer Patients Previously Treated with an Anthracycline and a Taxane: An Interim Analysis. Clinical Breast Cancer, Apr. 2001, vol. 2, No. 1 pp. 47-51.
Sukhai et al., Lysosomal disruption preferentially targets acute myeloid leukemia cells and progenitors. J Clin Invest. Jan. 2013;123(1):315-28. doi:10.1172/JCI64180. Epub Dec. 3, 2012.
Van Tri Est et al., Downstream molecular determinants of response to 5-fluorouracil and antifolate thymidylate synthase inhibitors, Annals of Oncology, 2000, vol. 11, No. 4, pp. 385-391.
Voeller et al., Elevated Levels of Thymidylate Synthase Linked to Neoplastic Transformation of Mammalian Cells, Cell Cycle, Aug. 2004, vol. 3, No. 8, pp. 1005-1007.
Wahba et al., Direct Spectrophotometric Evidence for the Oxidation of Tetrahydrofolate during the Enzymatic Synthesis of Thymidylate. J Biological Chemistry, vol. Mar. 1961, vol. 236, pp. PC11-PC12.
Wahba et al., The Enzymatic Synthesis of Thymidylate. I. Early steps in the purification of thymidylate synthetase of *Escherichia coli*. J Biological Chemistry, Dec. 1962, vol. 237, No. 12, pp. 3794-3801.
Yan et al., Mefloquine induces cell death in prostate cancer cells and provides a potential novel treatment strategy in vivo . . . Oncol Lett. May 2013;5(5):1567-1571. Epub Mar. 15, 2013.
Yan et al., Mefloquine exerts anticancer activity in prostate cancer cells via ROSmediated modulation of Akt, ERK, JNK and AMPK signaling, Oncology Letters, 2013, vol. 5, pp. 1541-1545.

\* cited by examiner

I. Compound P + Everolimus (mTOR inhibitor)
1. MiaPaCa-2
   a. Ratio M
      12μM P: 0.1μM E
   b. Ratio A
      7.7μM P: 0.1μM E
   c. Ratio B
      3.5μM P: 0.1μM E
2. Panc-1
   a. Ratio M
      12μM P: 0.1μM E
   b. Ratio A
      7.7μM P: 0.1μM E
   c. Ratio B
      3.0μM P: 0.1μM E
3. T182
   a. Ratio M
      12μM P: 0.1μM E
4. E549
   a. Ratio M
      12μM P: 0.1μM E II. Compound P + MK-2206 (AKT inhibitor)
1. MiaPaCa-2
   a. Ratio M
      12μM P: 8μM MK
   b. Ratio A
      3.5μM P: 4μM MK
2. Panc-1
   a. Ratio M
      12μM P: 8μM MK
   b. Ratio A
      3.0μM P: 9μM MK
3. T182
   a. Ratio M
      12μM P: 8μM MK
4. E549
   a. Ratio M
      12μM P: 8μM MK III. Compound P + BEZ235 (Dual PI-3K/mTOR inhibitor)
1. MiaPaCa-2
   a. Ratio M
      12μM P: 0.2 BEZ
   b. Ratio A
      3.5μM P: 0.02 BEZ
   c. Ratio B
      3.5μM P: 0.2 BEZ
2. Panc-1
   a. Ratio M
      12μM P: 0.2 BEZ
   b. Ratio A
      4.6μM P: 0.06 BEZ
   c. Ratio B
      4.6 μM P: 0.2 BEZ
3. T182
   a. Ratio M
      12μM P: 0.2 BEZ
4. E549
   a. Ratio M
      12μM P: 0.2 BEZ

Figure 1

| Compound P + Everolimus | Compound P + MK-2206 | Compound P + BEZ-235 |
|---|---|---|
| 0.1µM Everolimus : | 4µM - 9µM MK-2206: | 0.02µM - 0.2µM BEZ235: |
| 3.0µM - 12 µM Compound P | 3.0µM - 12 µM Compound P | 3.5µM - 12 µM Compound P |

Figure 21

COMPOSITIONS FOR THE TREATMENT OF PANCREATIC CANCER AND USES THEREOF

CROSS-REFERENCE TO RELATED APPLICATIONS

This application is a national stage filing under 35 U.S.C. § 371 of international PCT application, PCT/US2016/037731, filed Jun. 16, 2016, which claims the benefit of U.S. Provisional Application Ser. No. 62/183,831, filed Jun. 24, 2015, the disclosure of each of which is hereby incorporated by reference in its entirety, including all figures, tables and amino acid or nucleic acid sequences.

BACKGROUND OF THE INVENTION

Cancer is the second most prevalent cause of death in the United States and is a complex disease arising after a selection process for cells with acquired functional capabilities, such as limitless proliferative potential and metastatic capabilities. The subject application provides a novel combination therapy that targets cancer at the PI3K/AKT/mTOR pathway, which is constitutively activated in many types of cancers. The disclosed combination therapy has, surprisingly, been found to be effective in the treatment of cancer, particularly breast cancer, prostate cancer, multiple myeloma, hepatocyte carcinoma, lung cancer, non-small cell lung carcinoma, colorectal cancer, melanoma and/or pancreatic cancer.

BRIEF SUMMARY OF THE INVENTION

The subject application provides compositions comprising inhibitors of PI3K, AKT and/or mTOR, one or more 4-quinolinemethanols and a pharmaceutically acceptable excipient. These compositions can contain subtherapeutic amounts of each active ingredient (PI3K, AKT, mTOR, one or more 4-quinolinemethanols and various combinations thereof). The compositions provided by the subject application can be used for the treatment of various forms of cancer, such as breast cancer, prostate cancer, multiple myeloma, hepatocyte carcinoma, brain cancer, lung cancer, non-small cell lung carcinoma, colorectal cancer, melanoma and/or pancreatic cancer.

BRIEF DESCRIPTION OF THE DRAWINGS

FIG. 1: Outline of Compound P+Ras Effector Inhibitor Experiments.
FIG. 21: Summary Of Ratio Ranges for PDAC Cell Lines.

BRIEF DESCRIPTION OF THE TABLES

Figure 2:
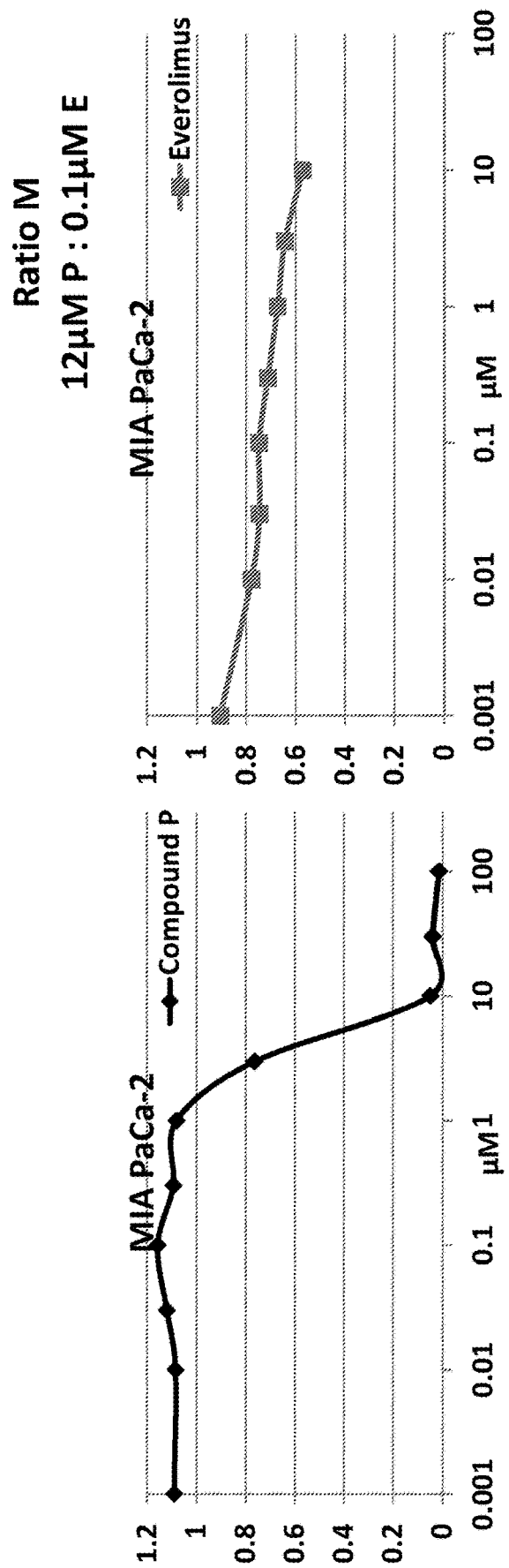
FIG. 2: Compound P+Everolimus MIA PaCa-2.
Figure 2:
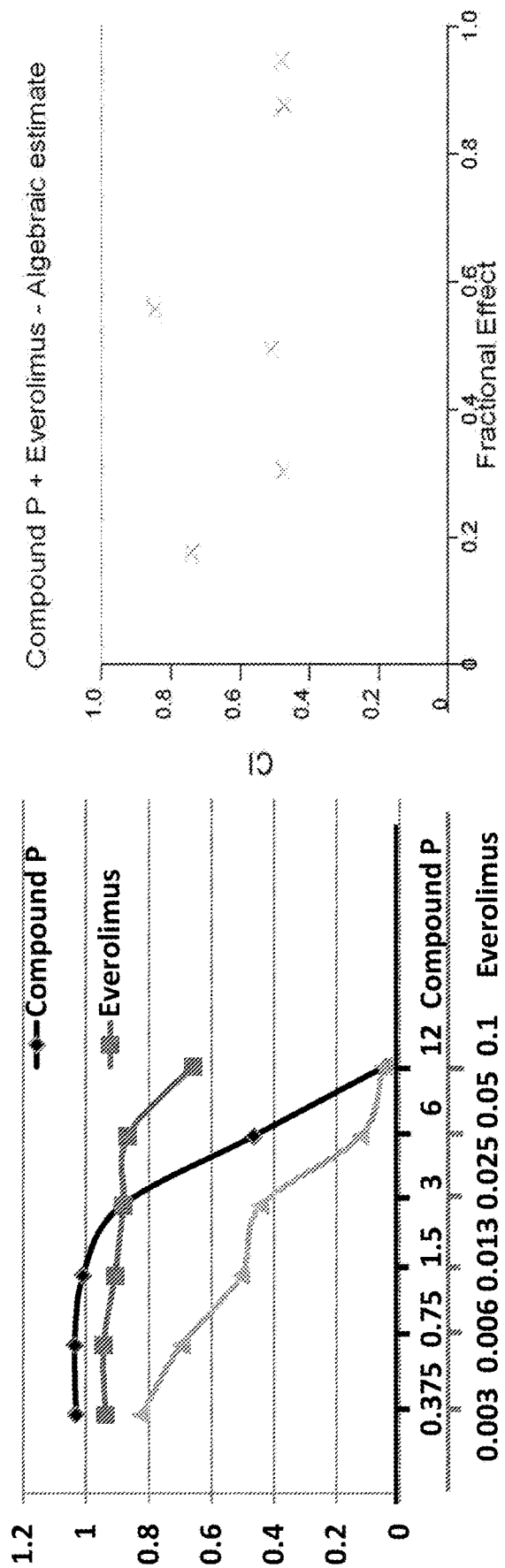
Figure 3:
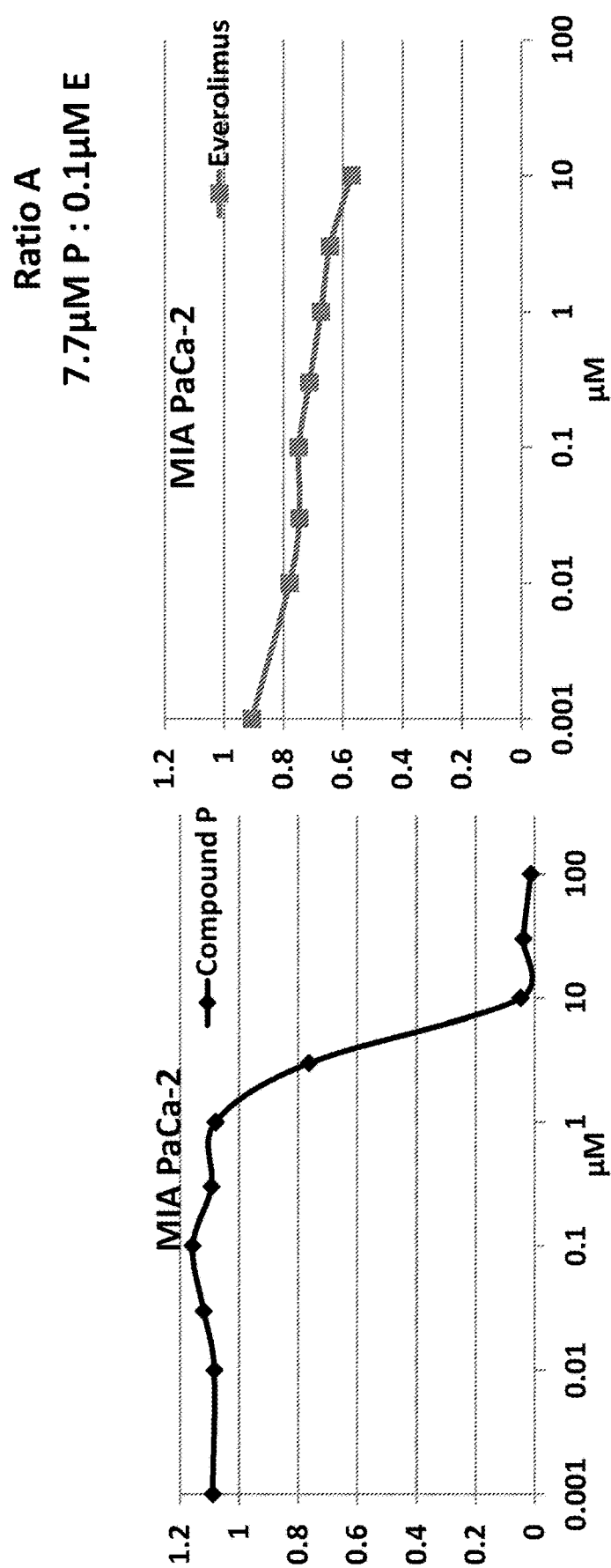
FIG. 3: Compound P+Everolimus MIA PaCa-2.
Figure 3:
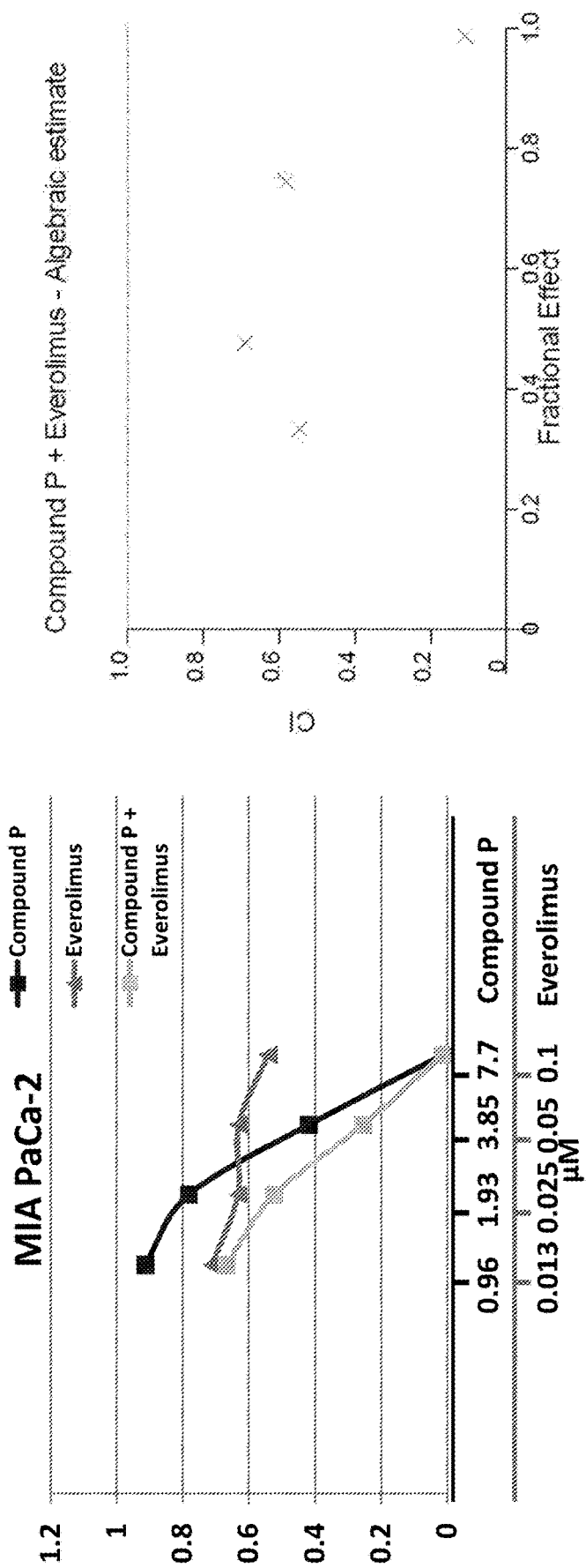
Figure 4:
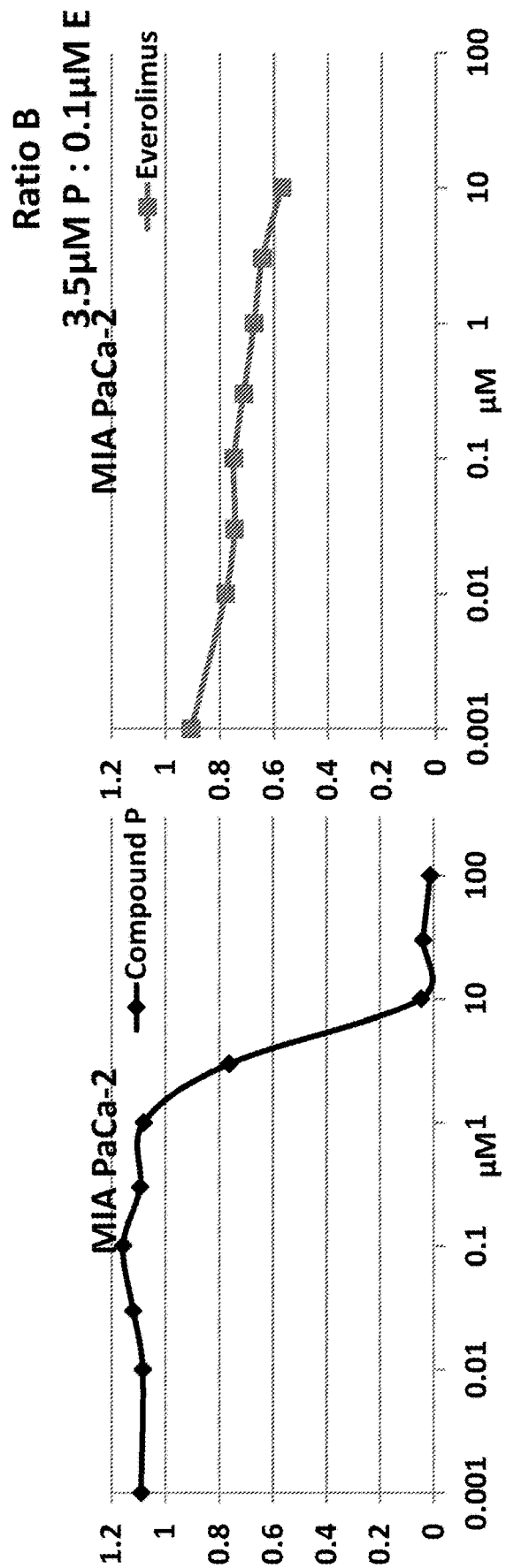
FIG. 4: Compound P+Everolimus MIA PaCa-2.
Figure 4:
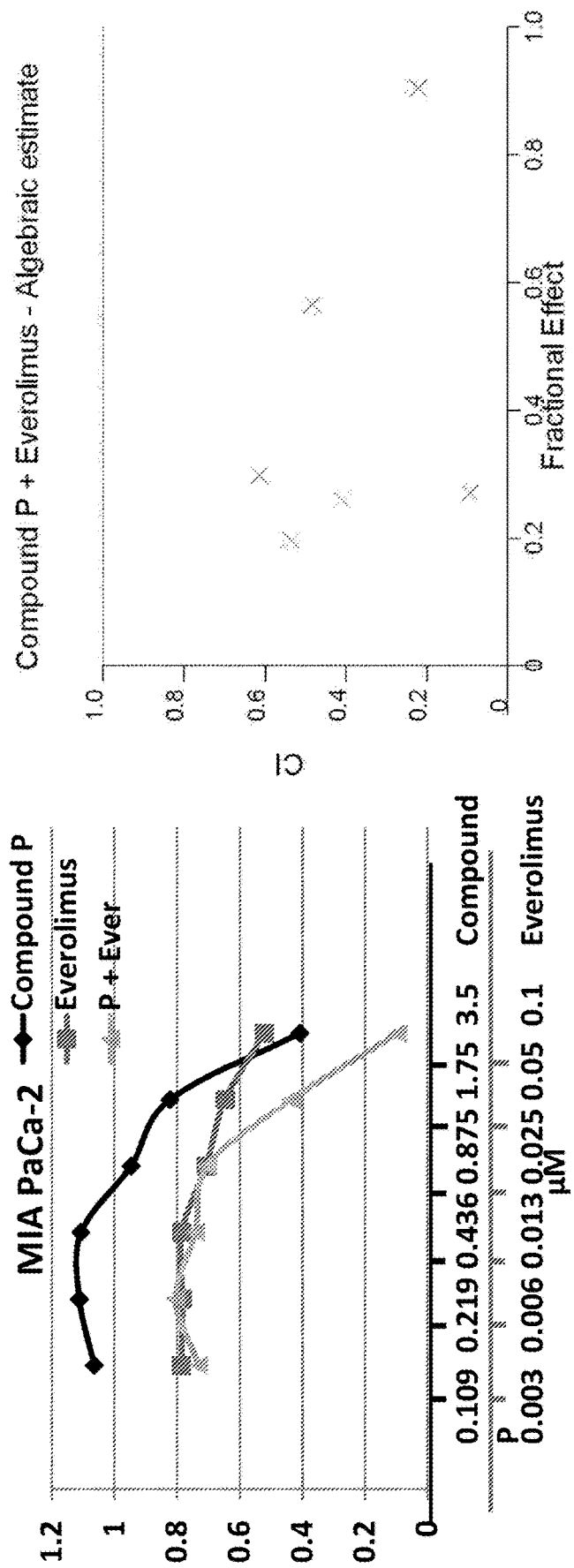
Figure 5:
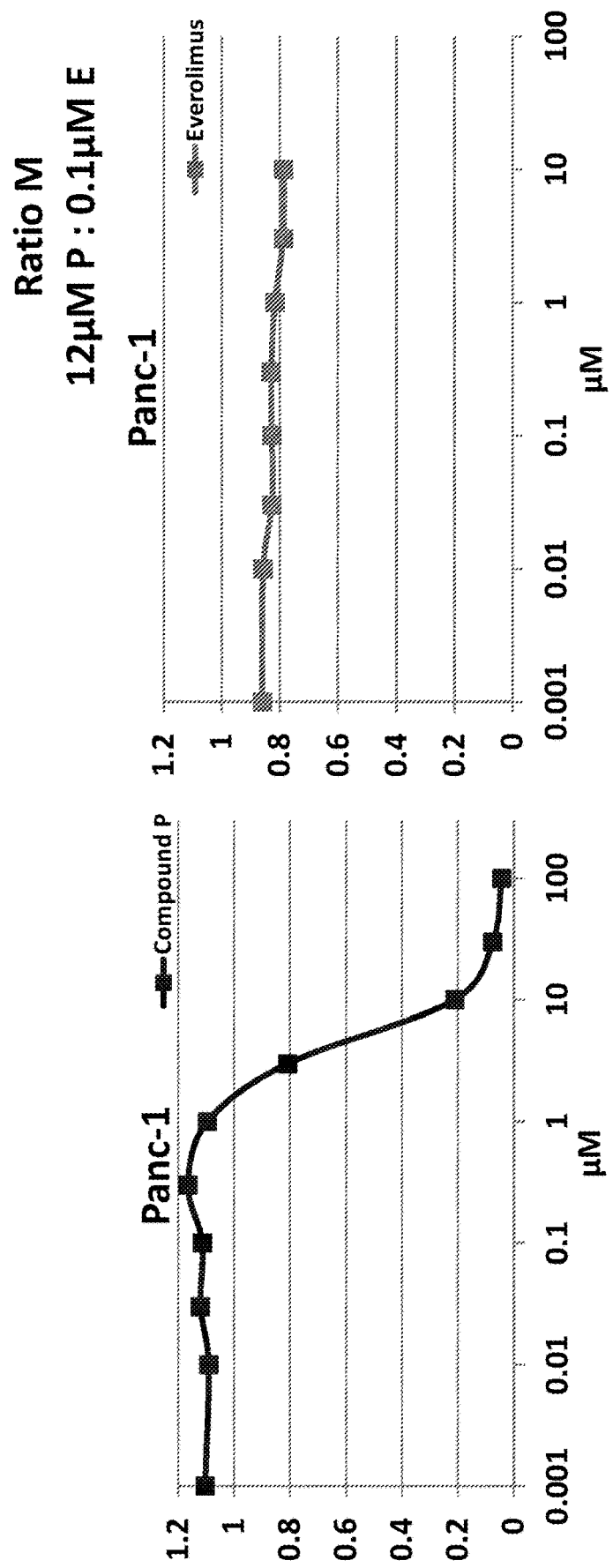
FIG. 5: Compound P+Everolimus Panc-1.
Figure 5:
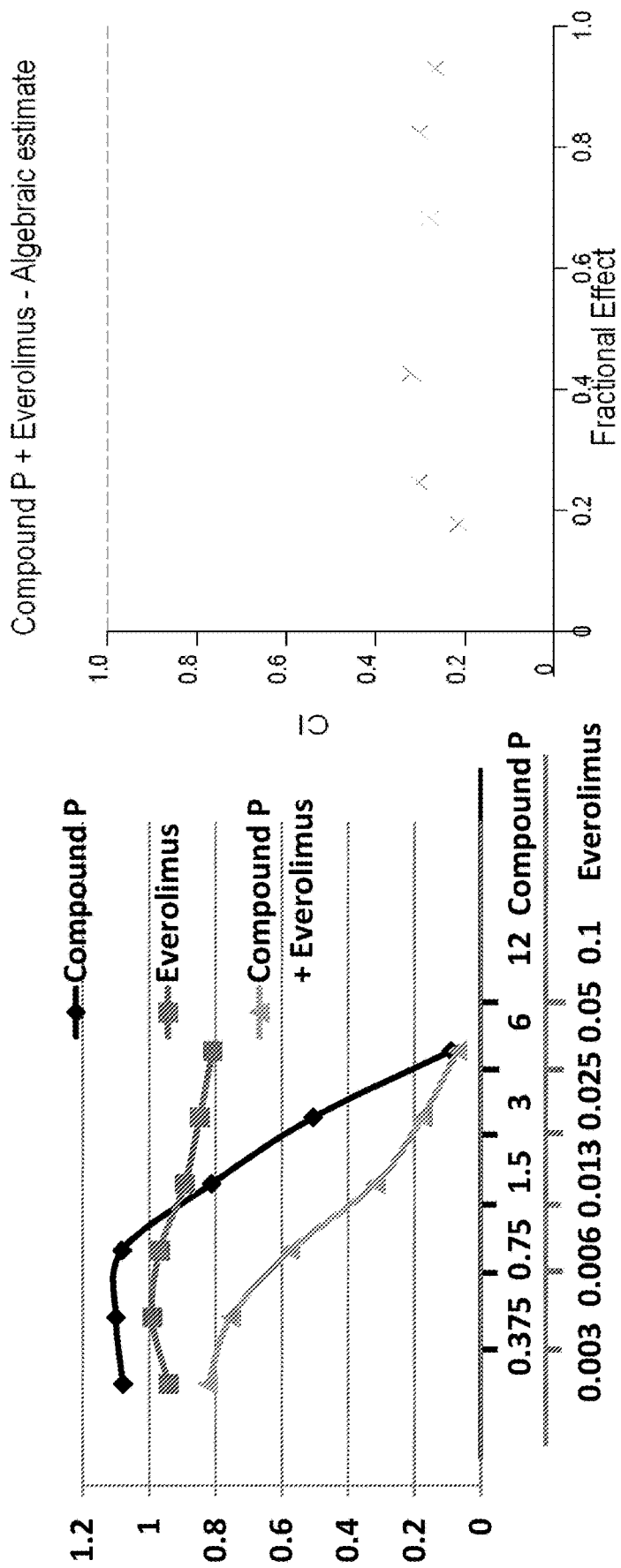
Figure 6:
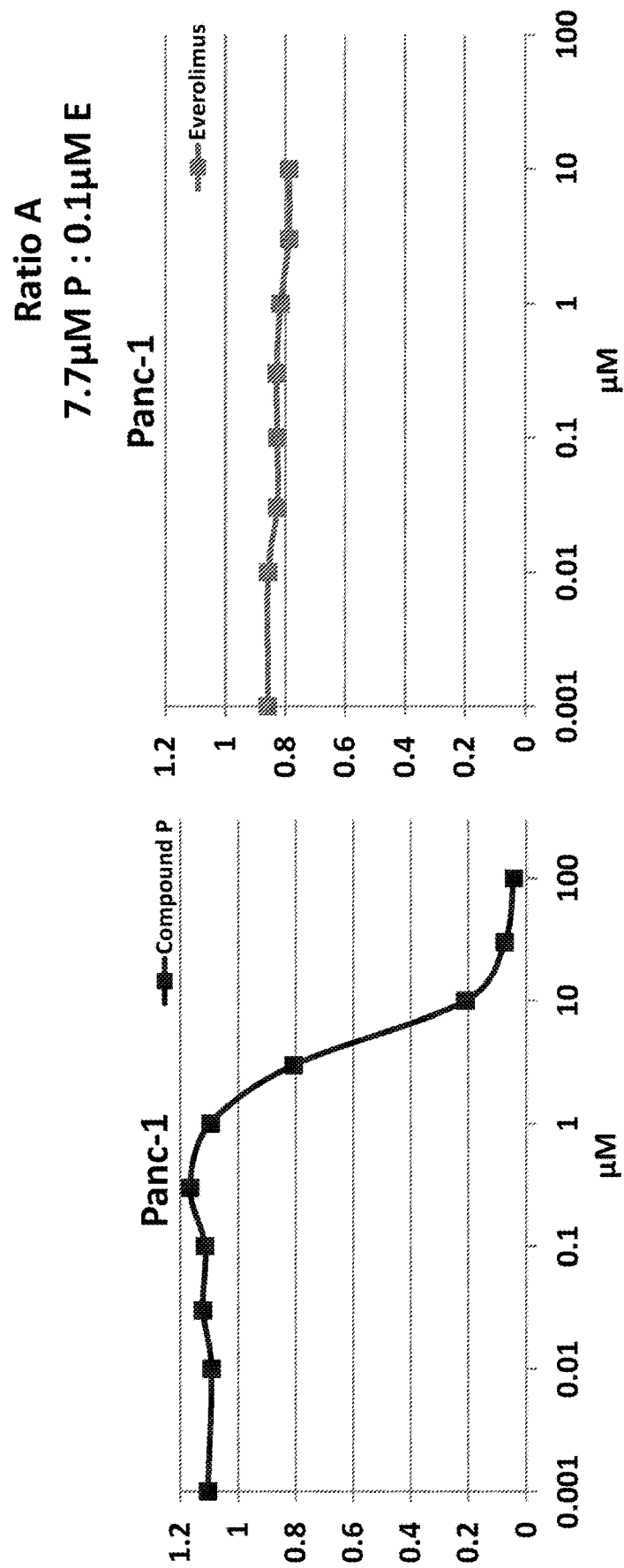
FIG. 6: Compound P+Everolimus Panc-1.
Figure 6:
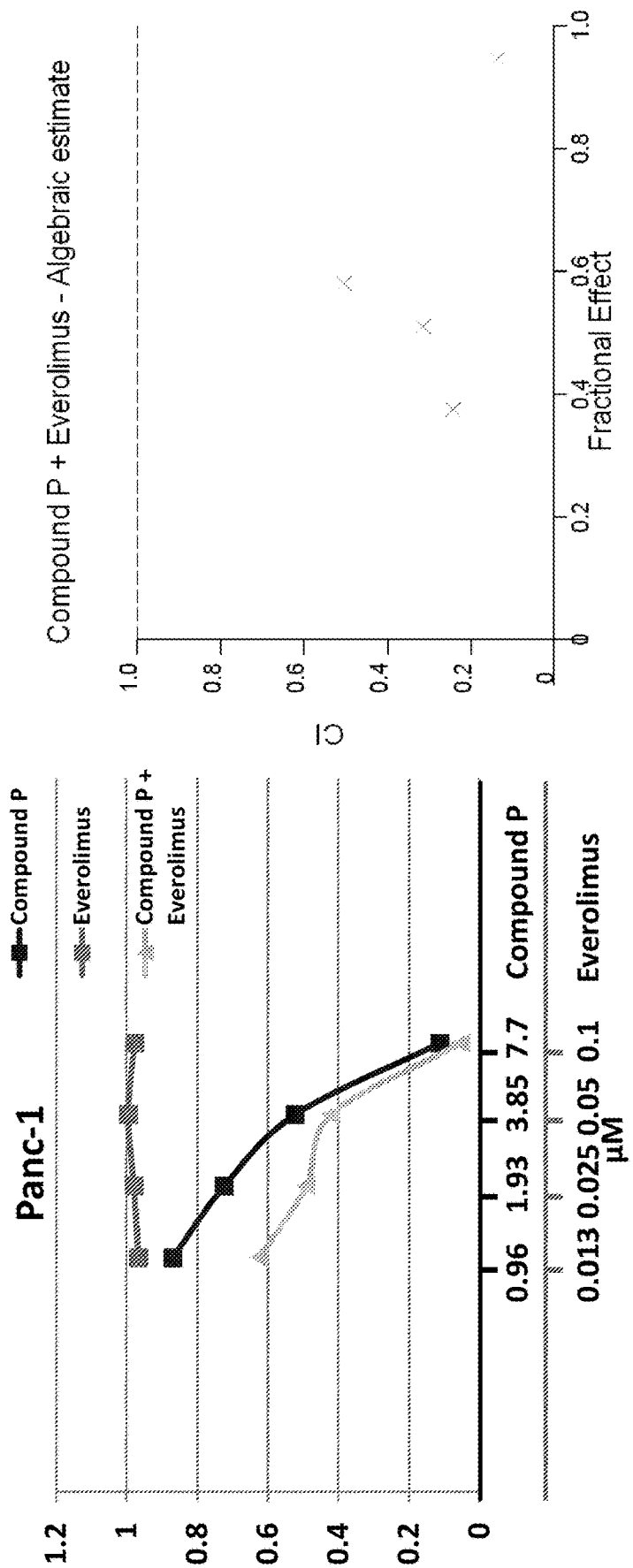
Figure 7:
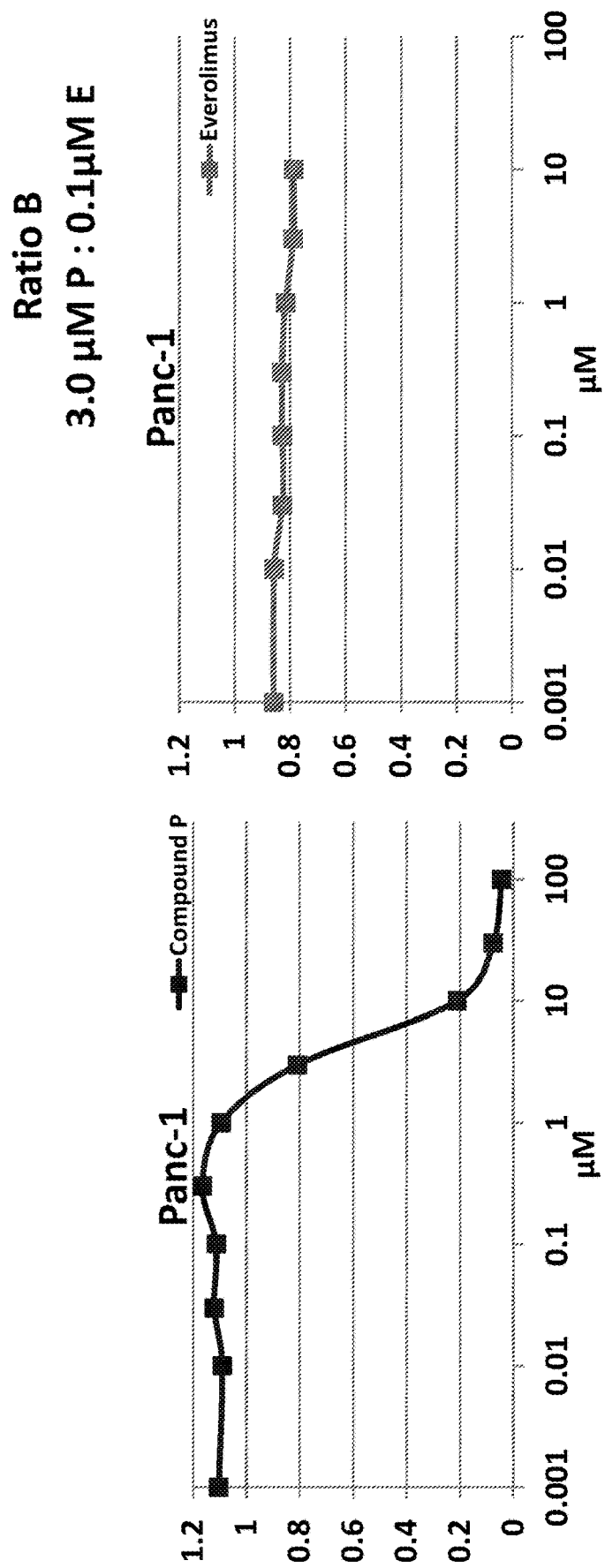
FIG. 7: Compound P+Everolimus Panc-1.
Figure 7:
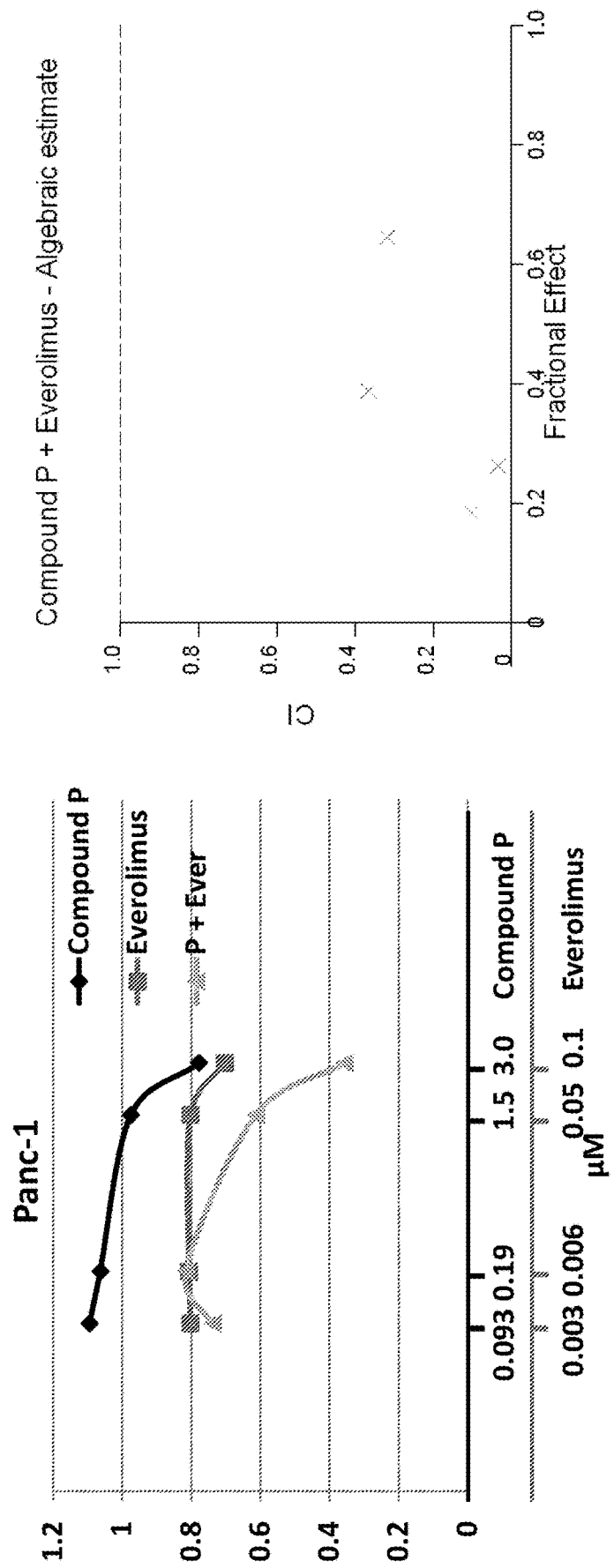
Figure 8:
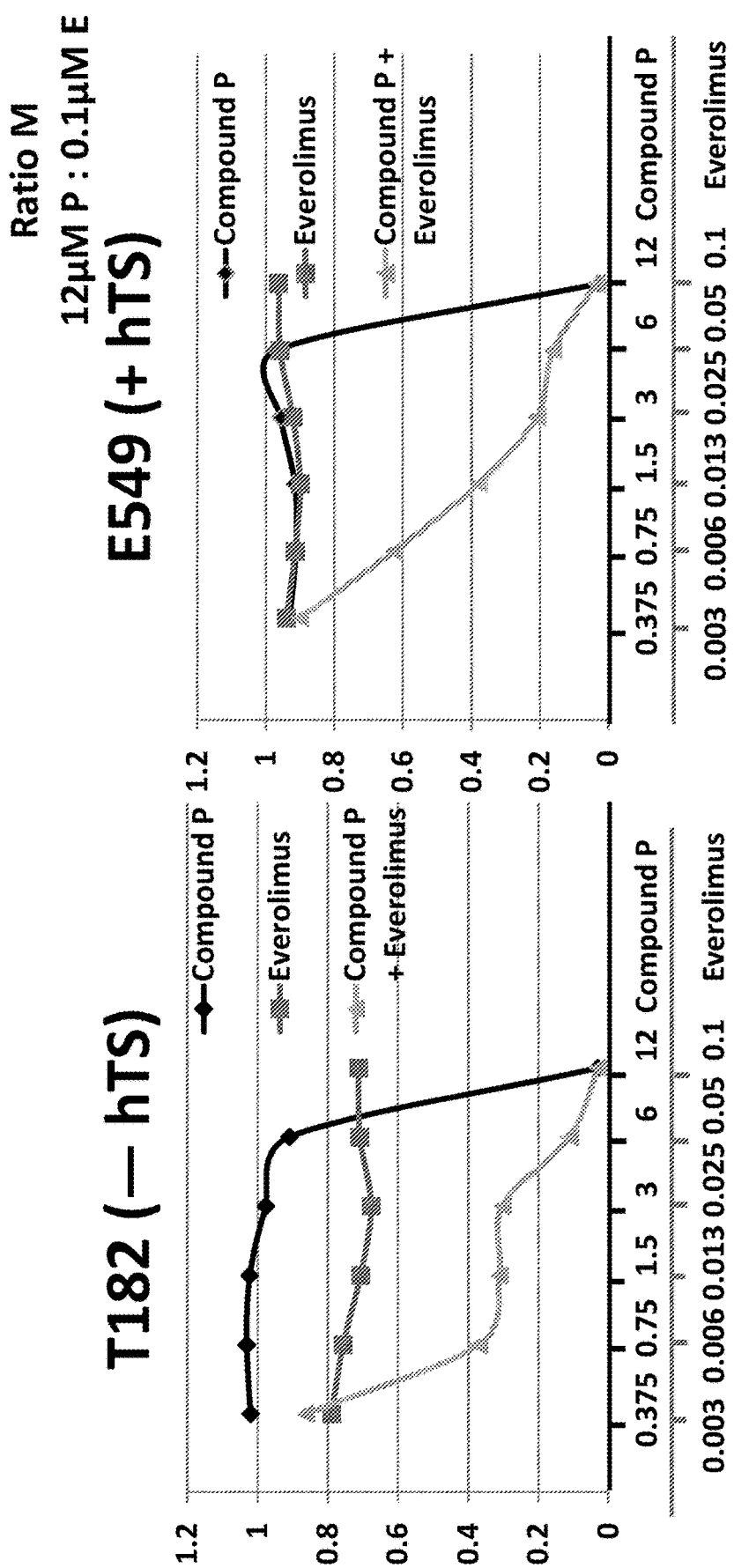
FIG. 8: Compound P+Everolimus (mTOR inhibitor) in Pancreatic Ductal Adenocarcinoma Cell Lines Derived from KRAS/PTEN Mutant Mouse Tumors.
Figure 9:
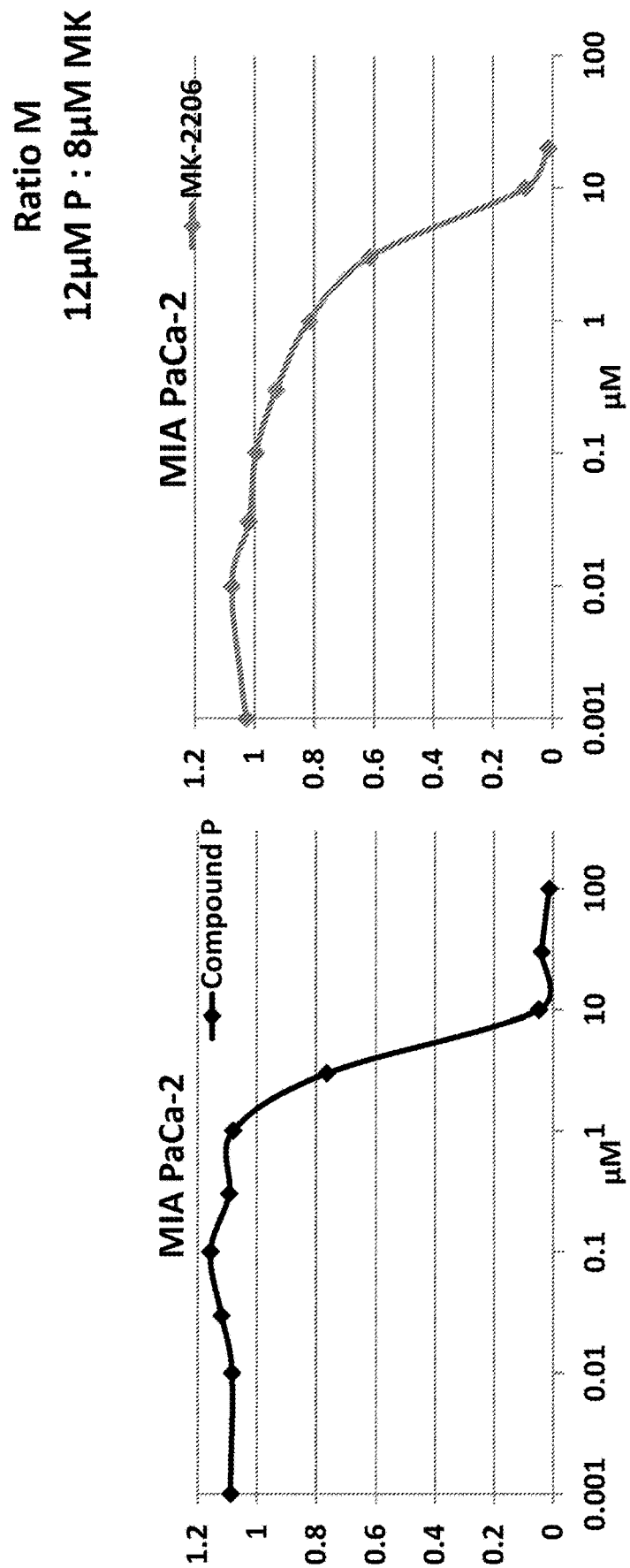
FIG. 9: Compound P+MK-2206 MIA PaCa-2.
Figure 9:
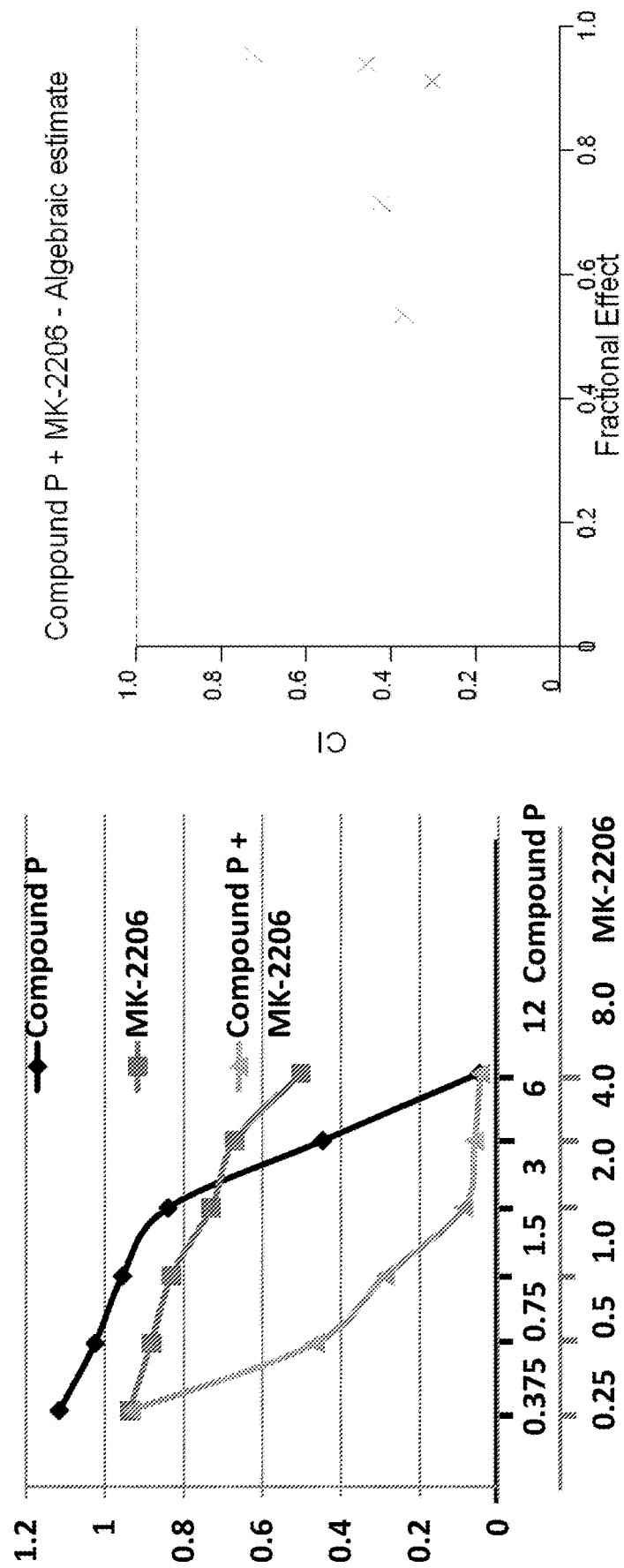
Figure 10:
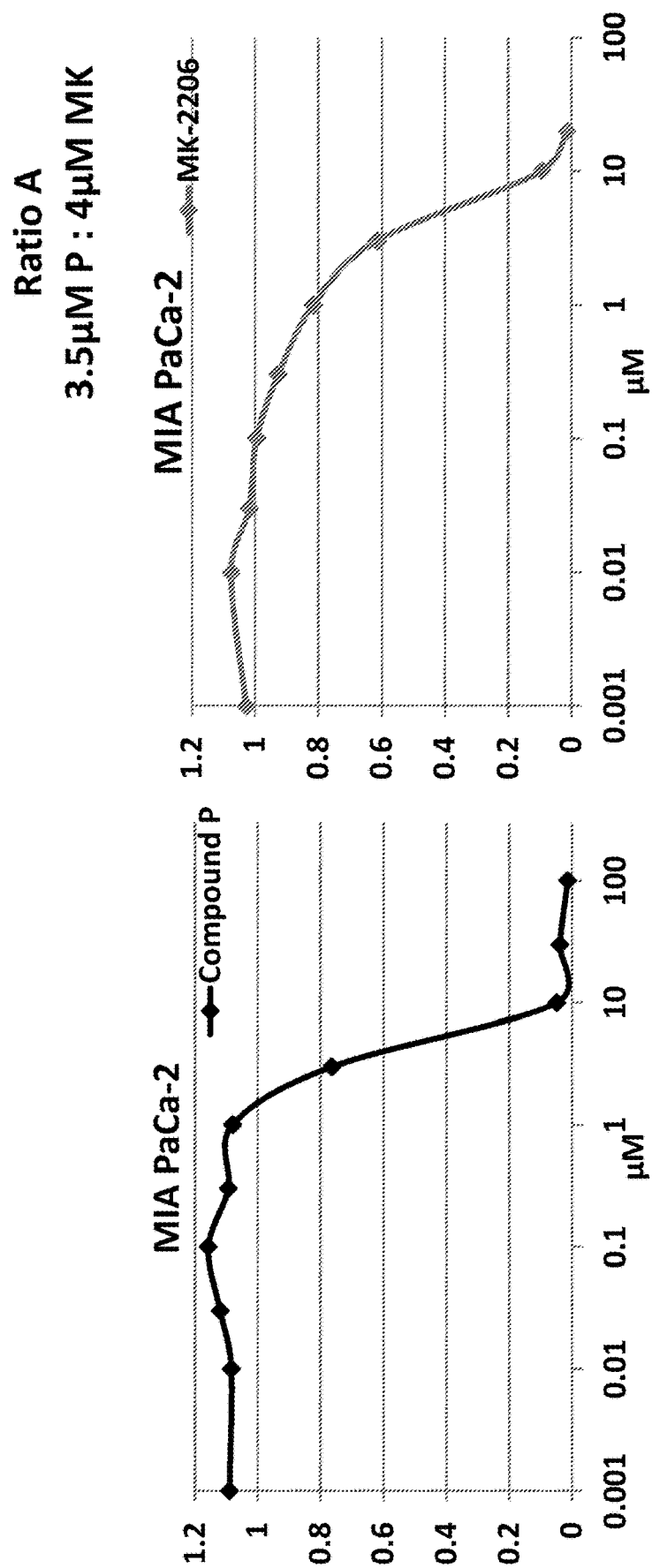
FIG. 10: Compound P+MK-2206 MIA PaCa-2.
Figure 10:
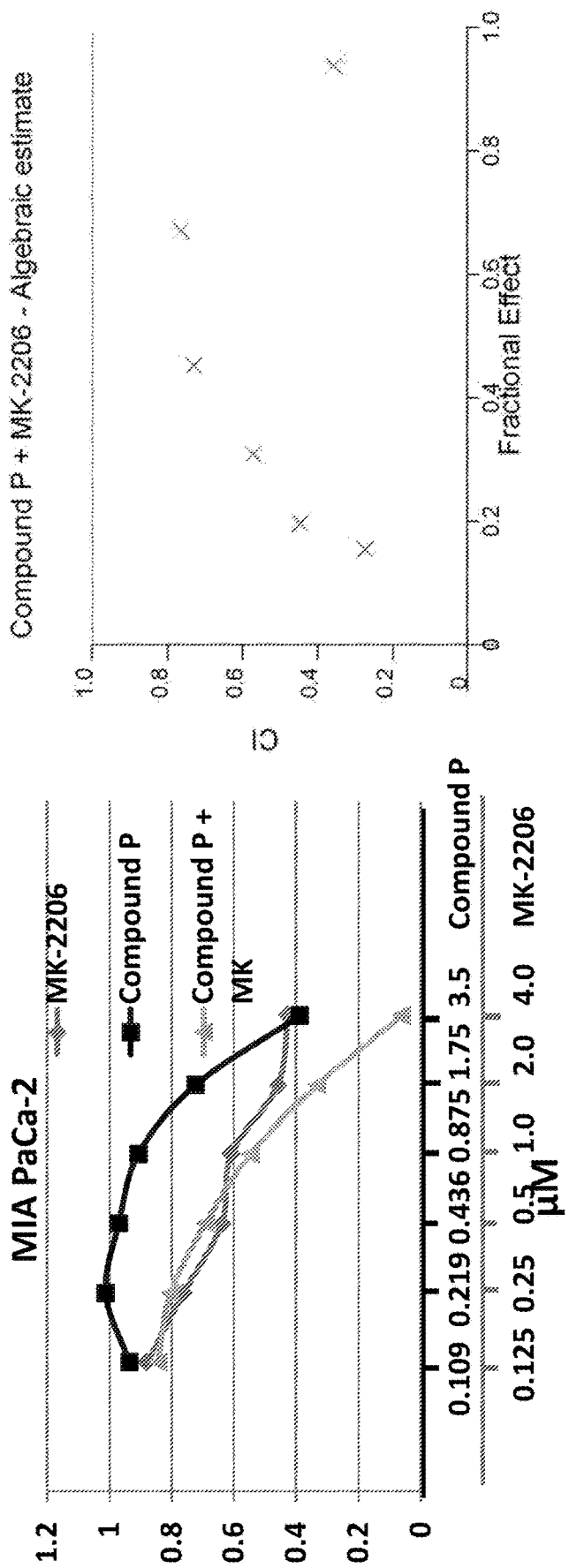
Figure 11:
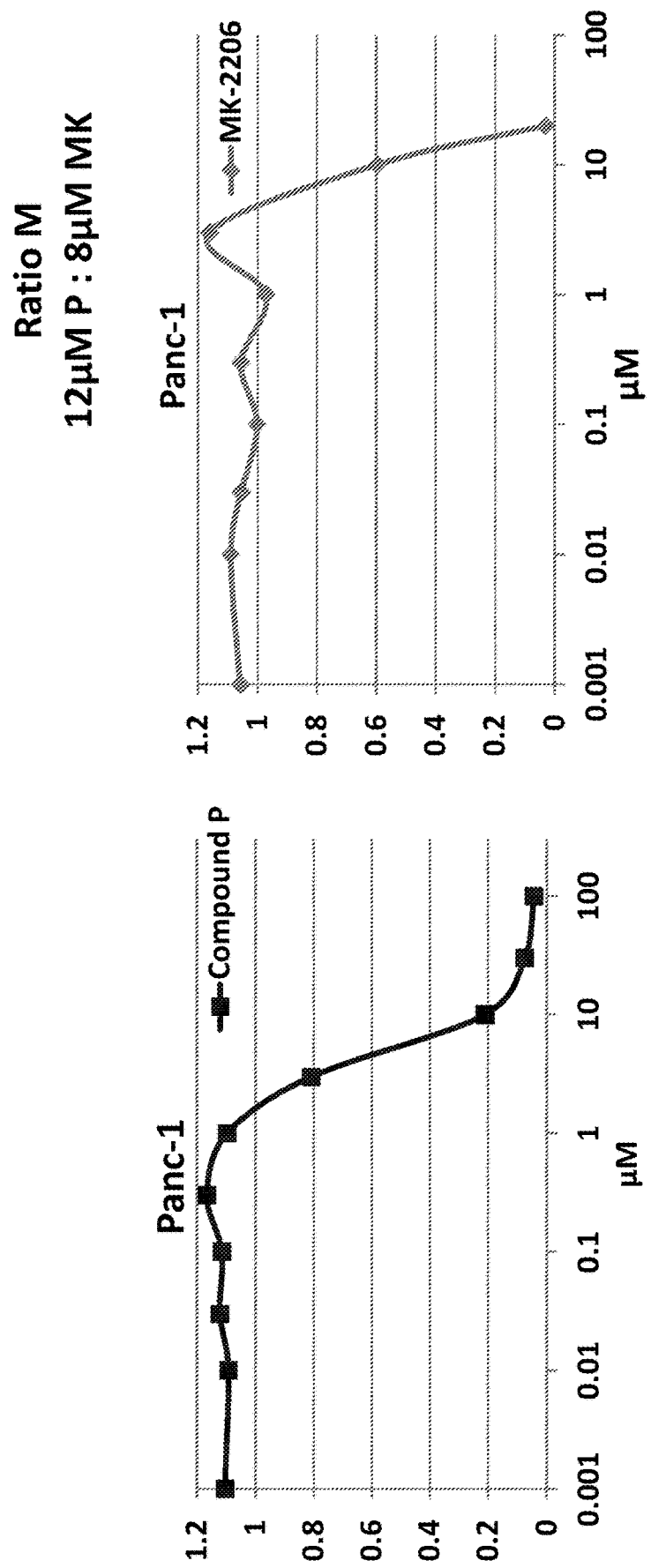
FIG. 11: Compound P+MK-2206 Panc-1.
Figure 11:
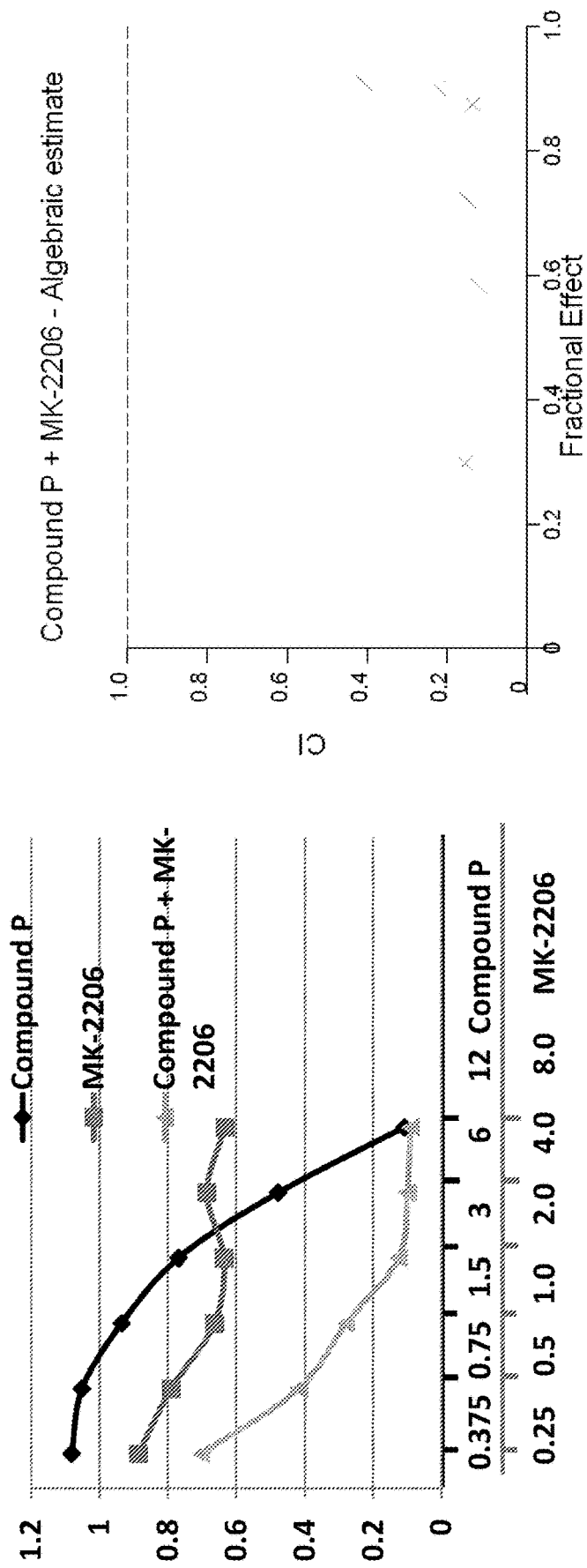
Figure 12:
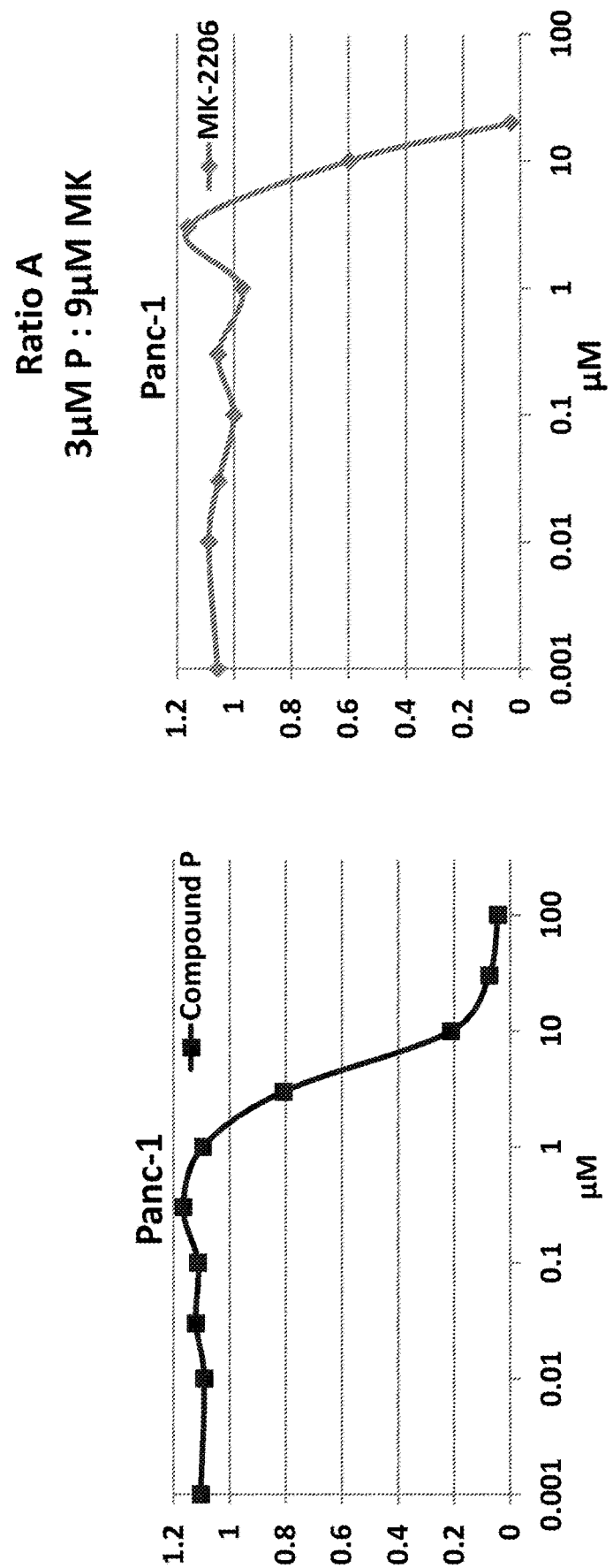
FIG. 12: Compound P+MK-2206 Panc-1.
Figure 12:
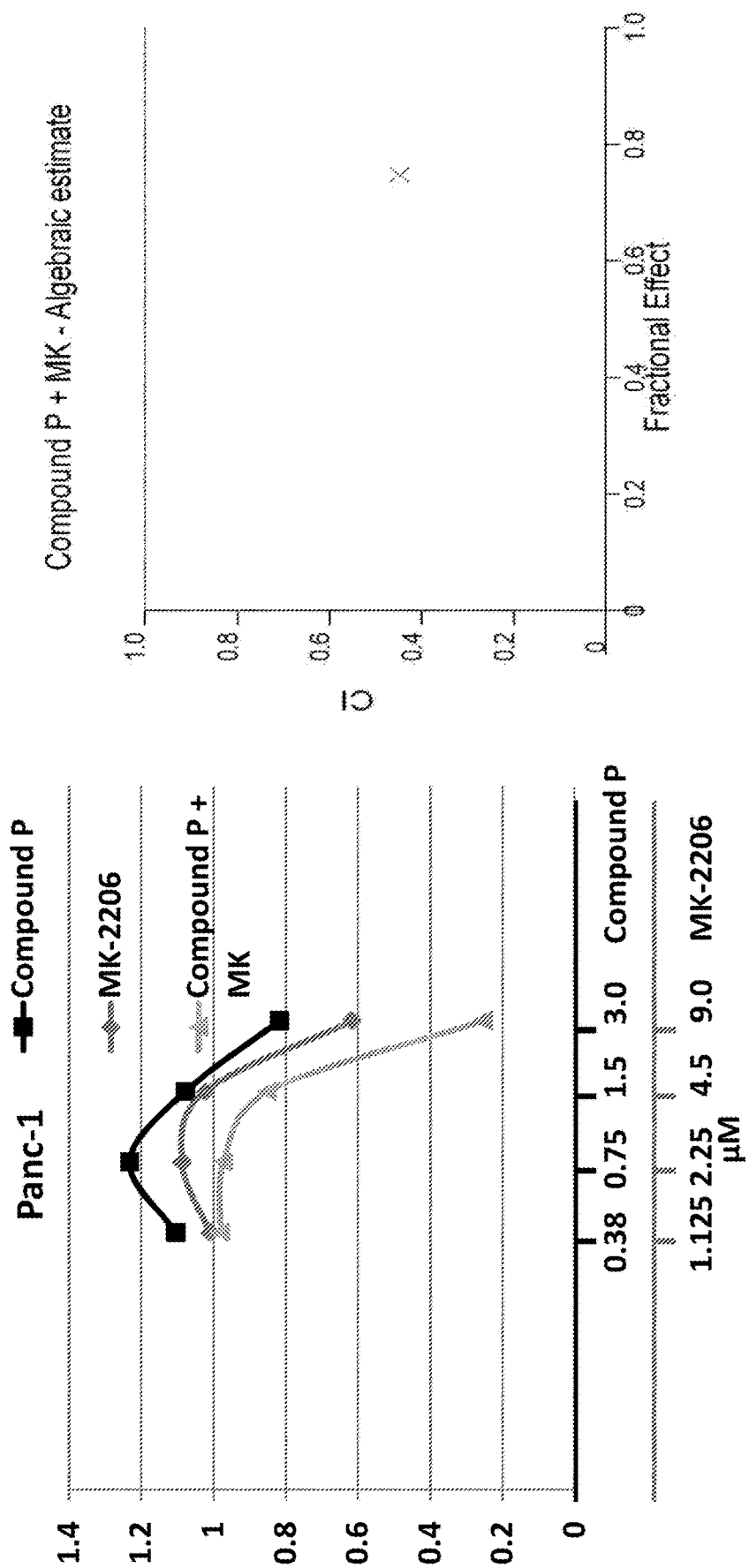
Figure 13:
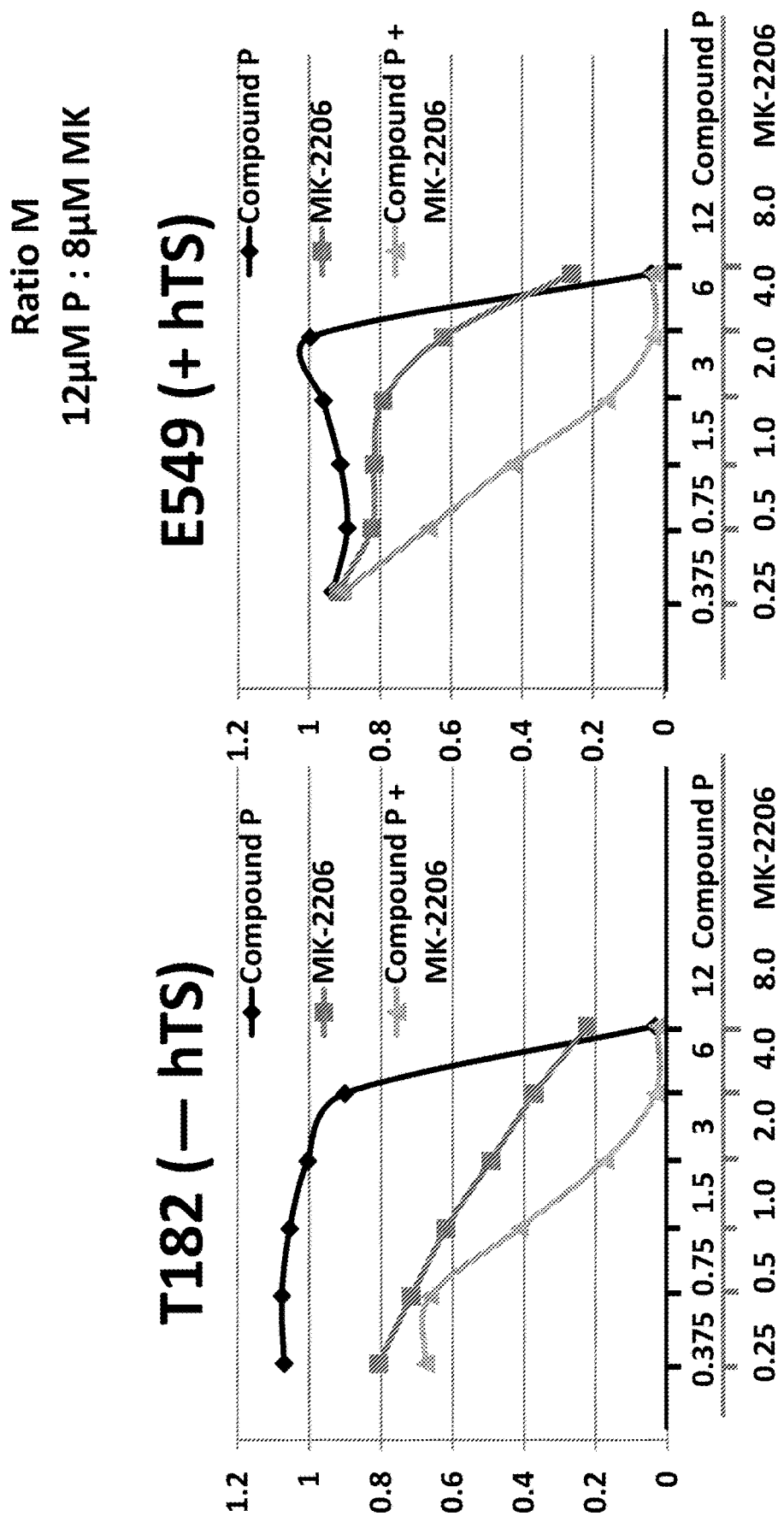
FIG. 13: Compound P+MK-2206 (AKT inhibitor) in Pancreatic Ductal Adenocarcinoma Cell Lines Derived from KRAS/PTEN Mutant Mouse Tumors.
Figure 14:
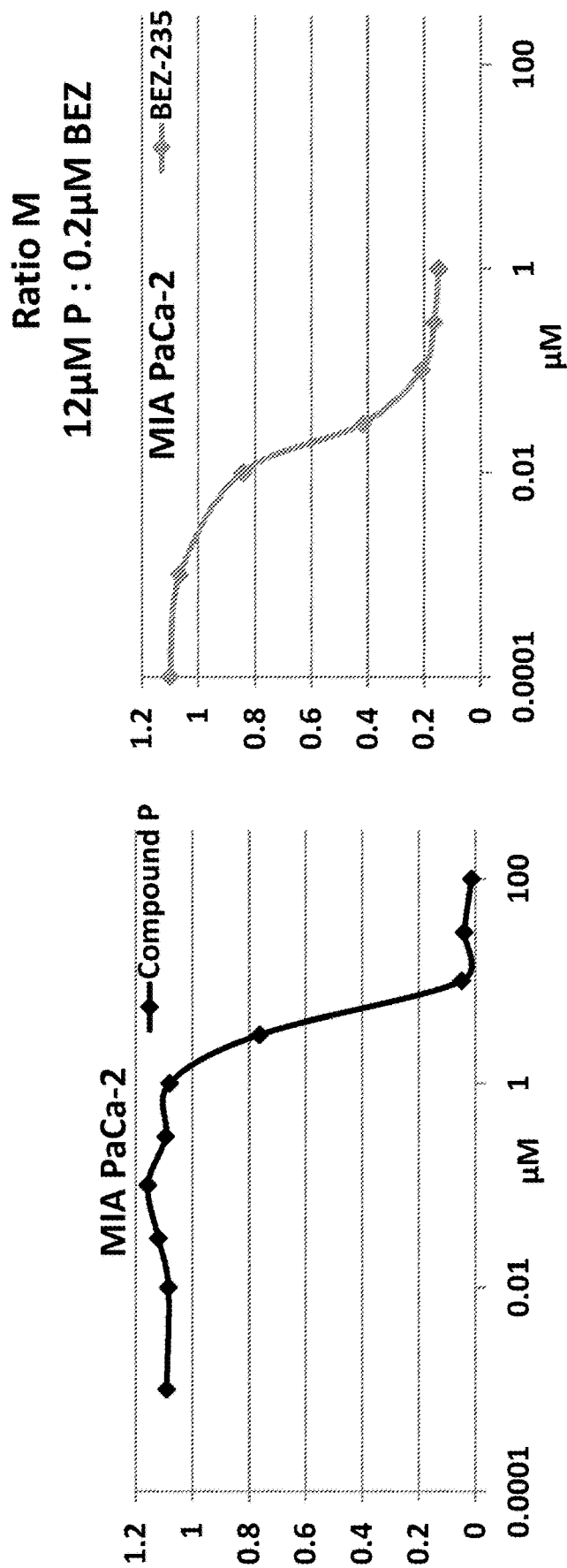
FIG. 14: Compound P+BEZ-235 MIA PaCa-2.
Figure 14:
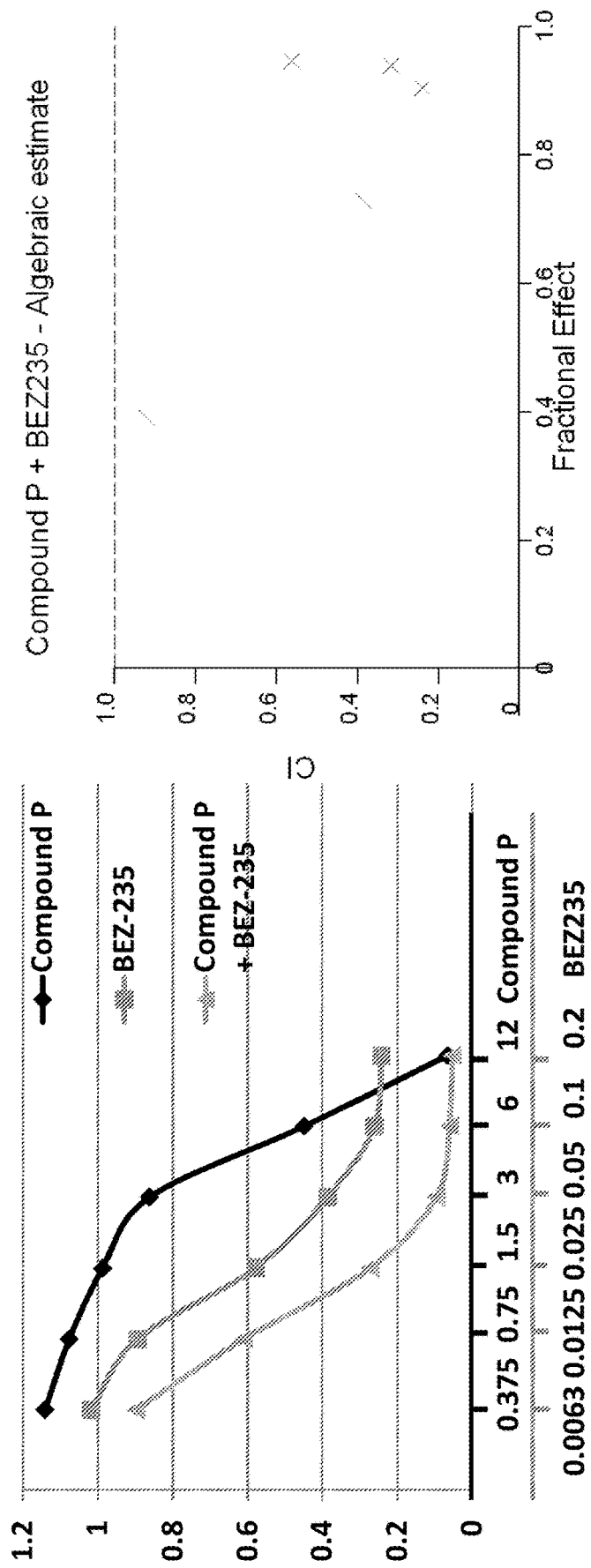
Figure 15:
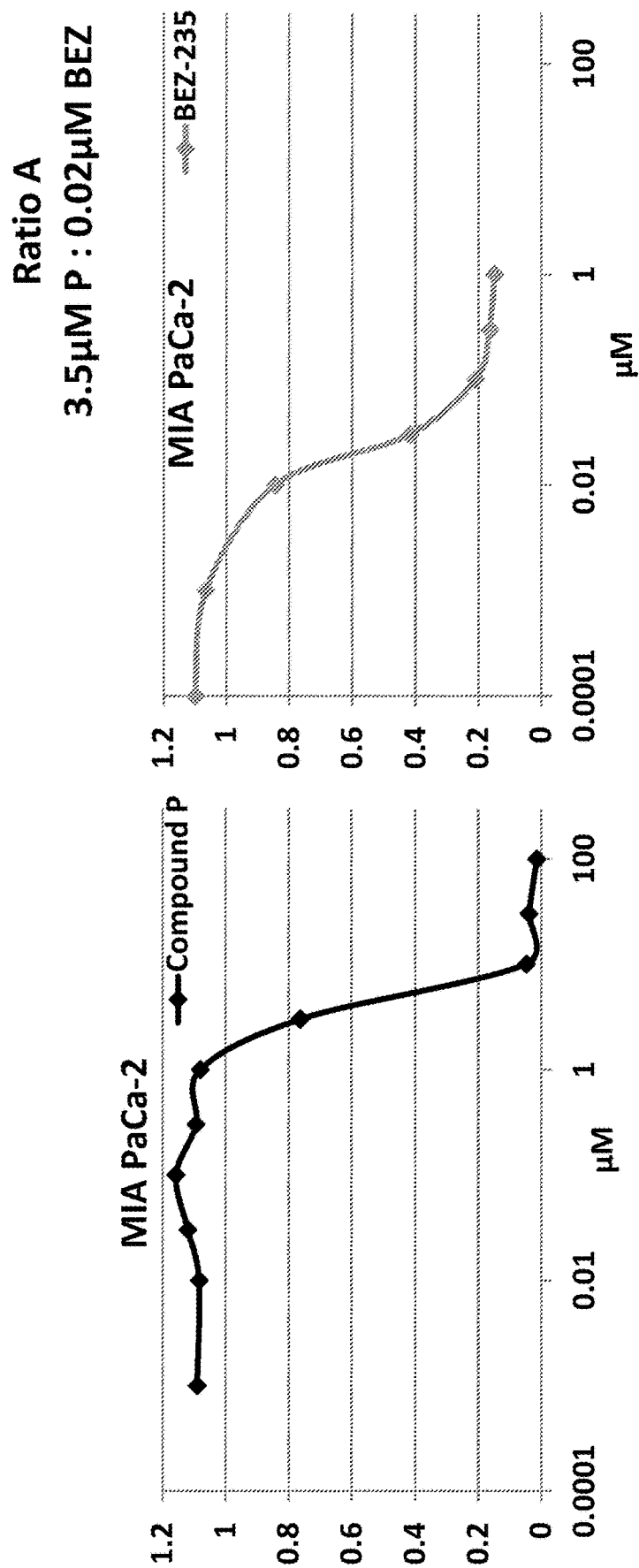
FIG. 15: Compound P+BEZ-235 MIA PaCa-2.
Figure 15:
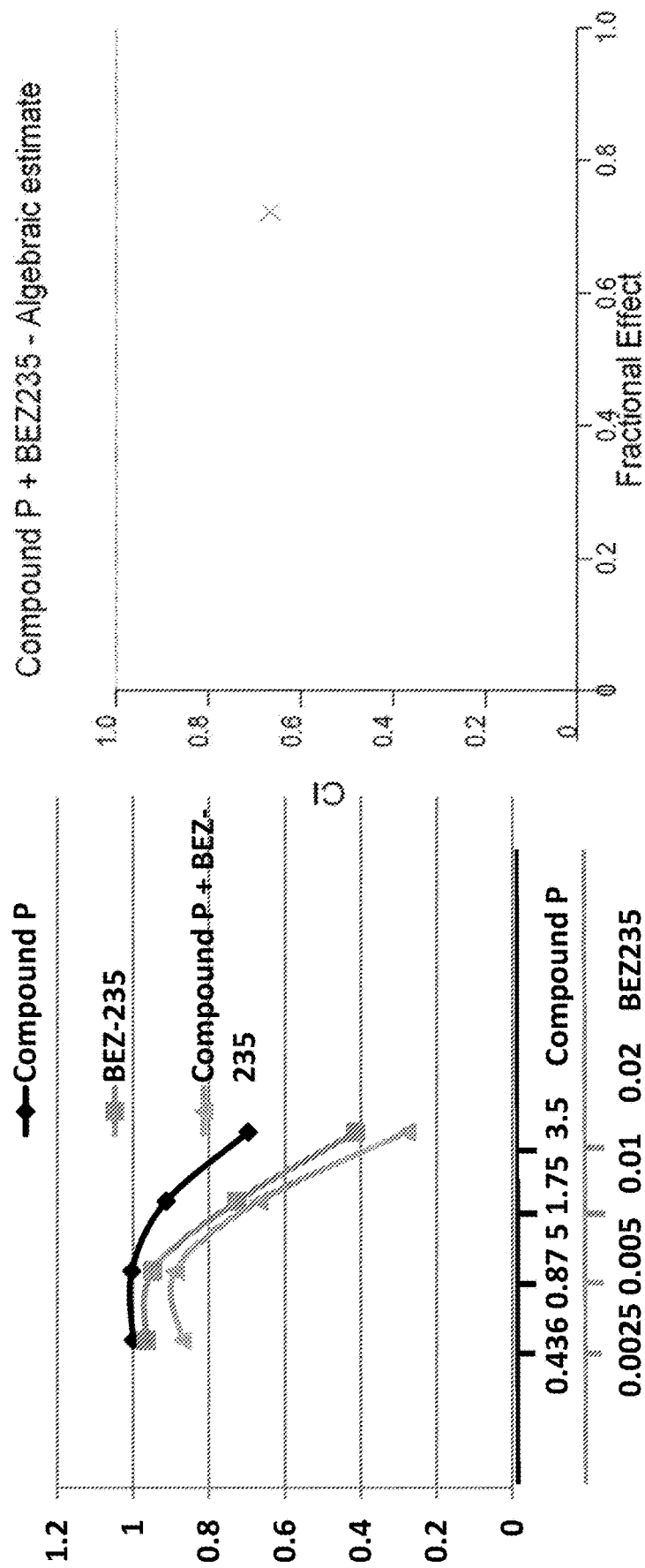
Figure 16:
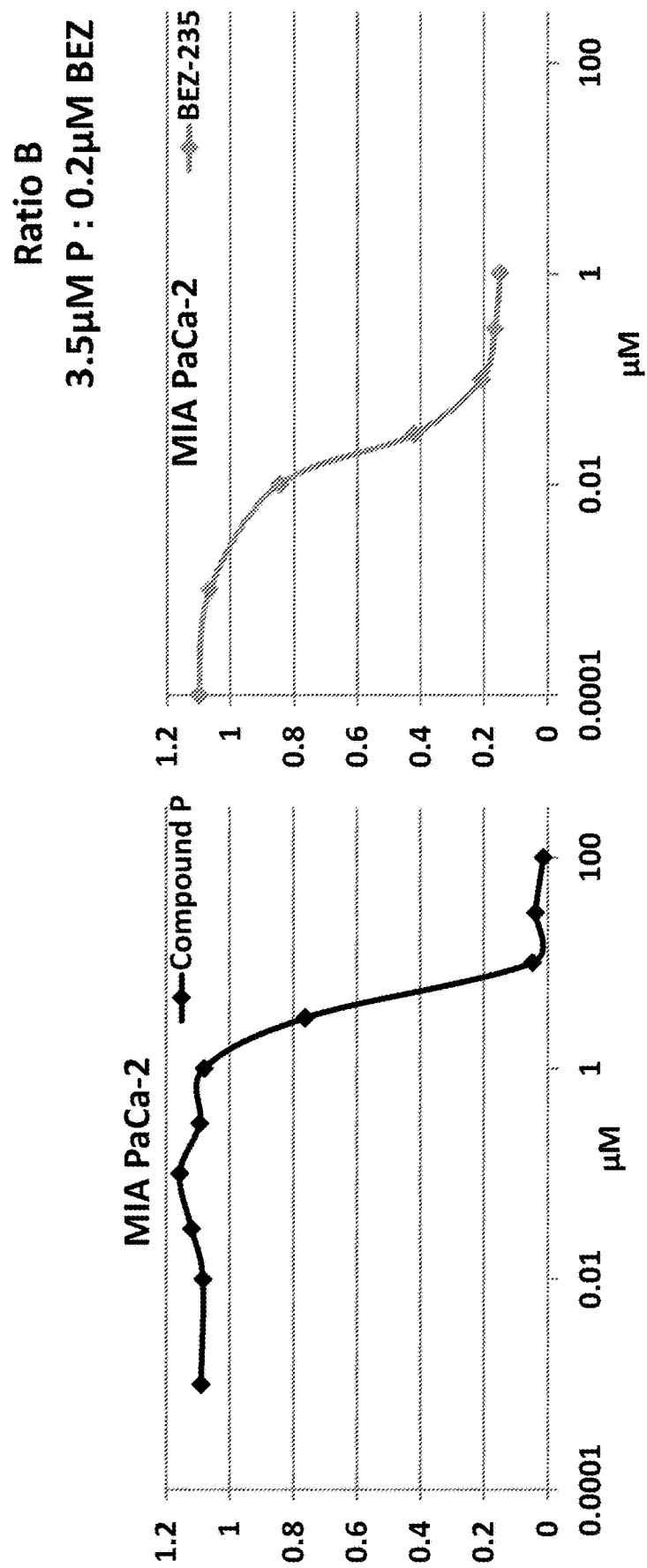
FIG. 16: Compound P+BEZ-235 MIA PaCa-2.
Figure 16:
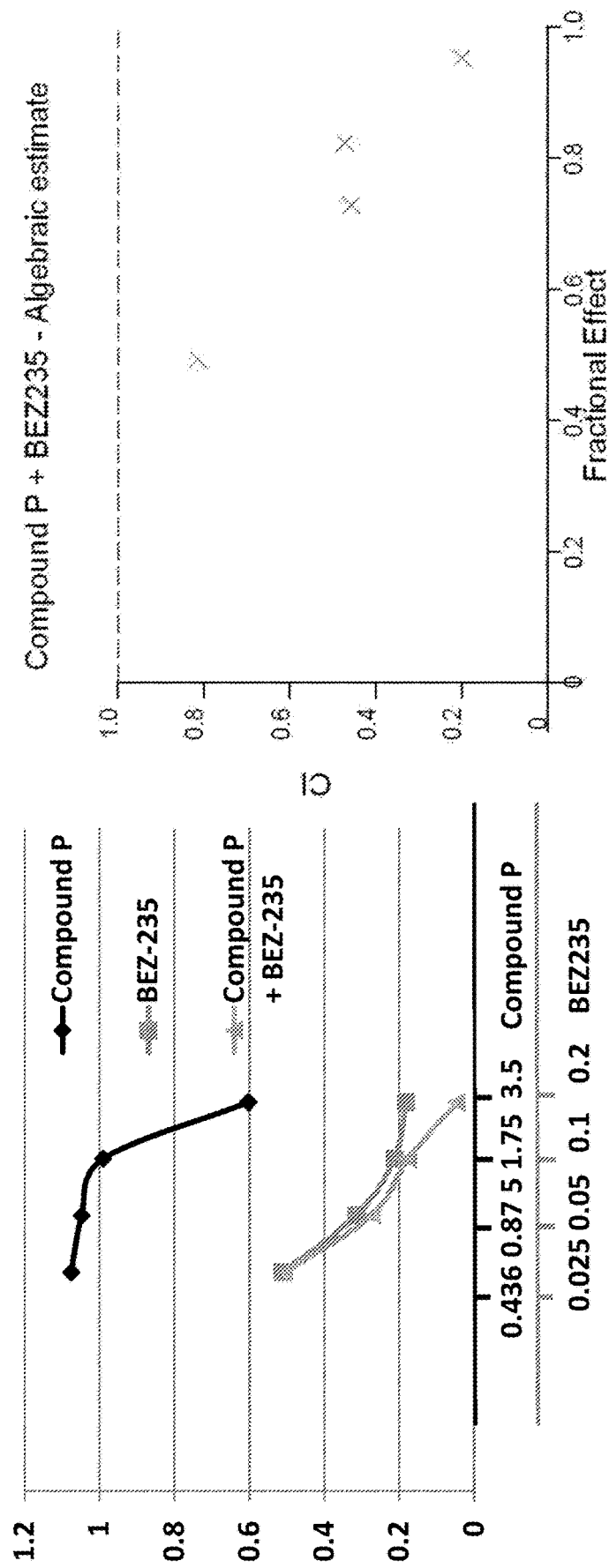
Figure 17:
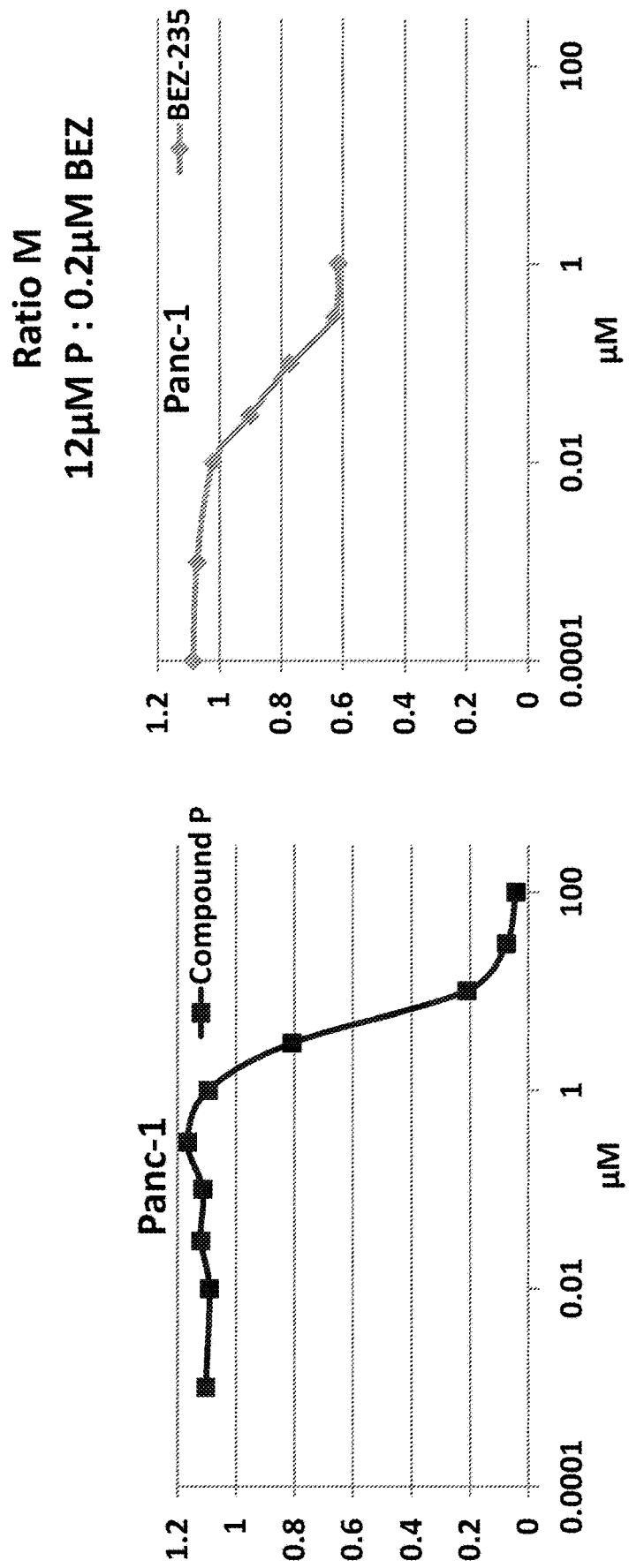
FIG. 17: Compound P+BEZ-235 Panc-1.
Figure 17:
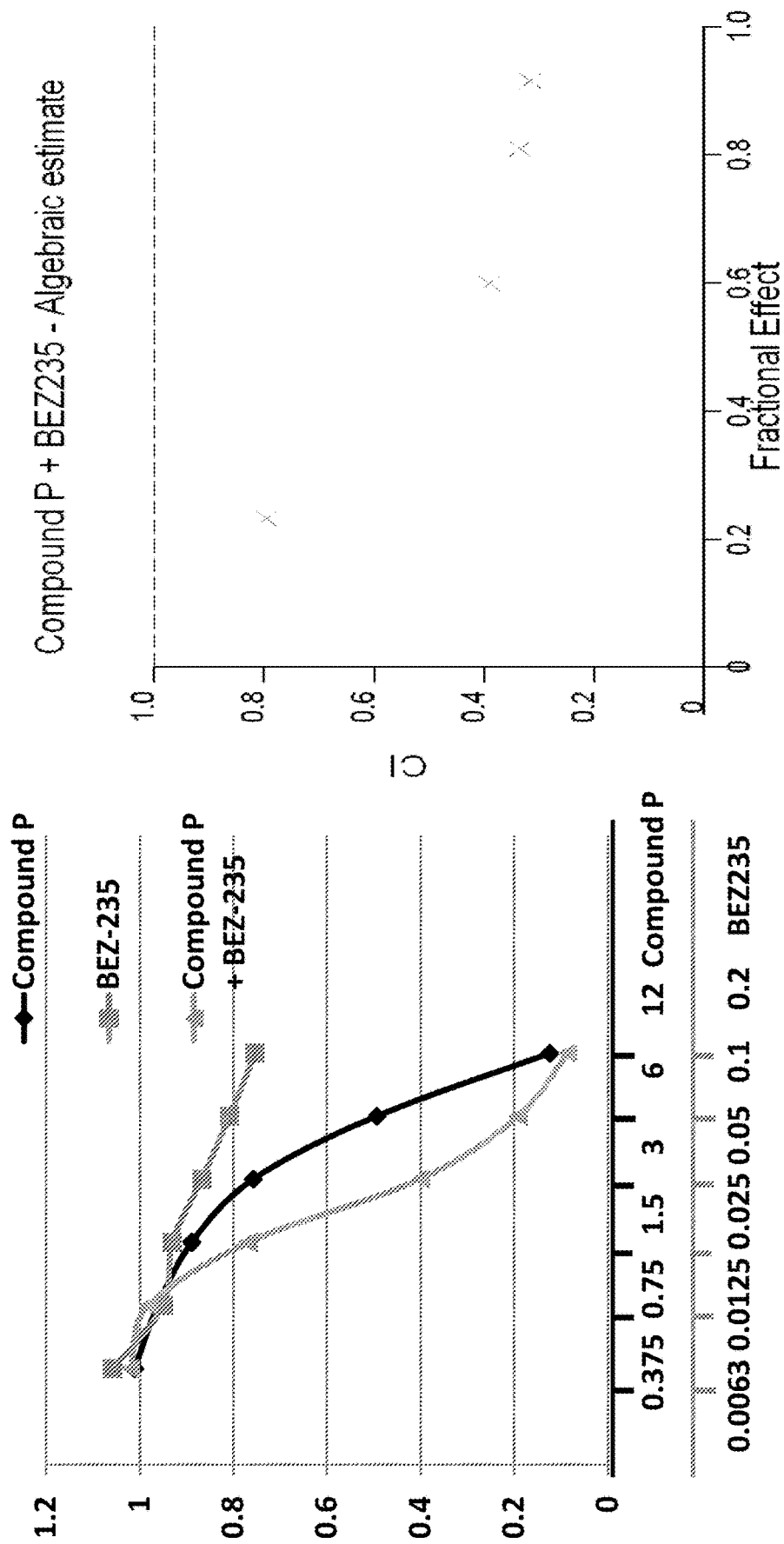
Figure 18:
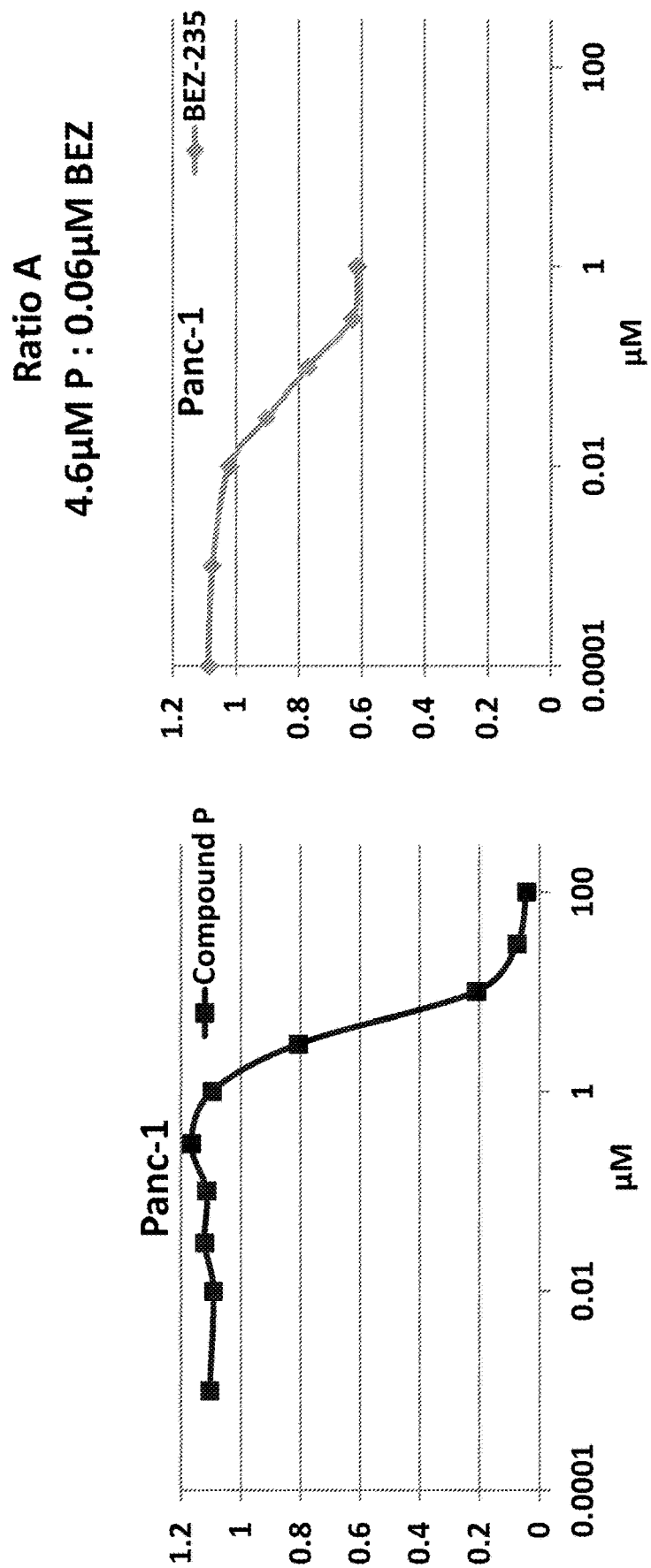
FIG. 18: Compound P+BEZ-235 Panc-1.
Figure 18:
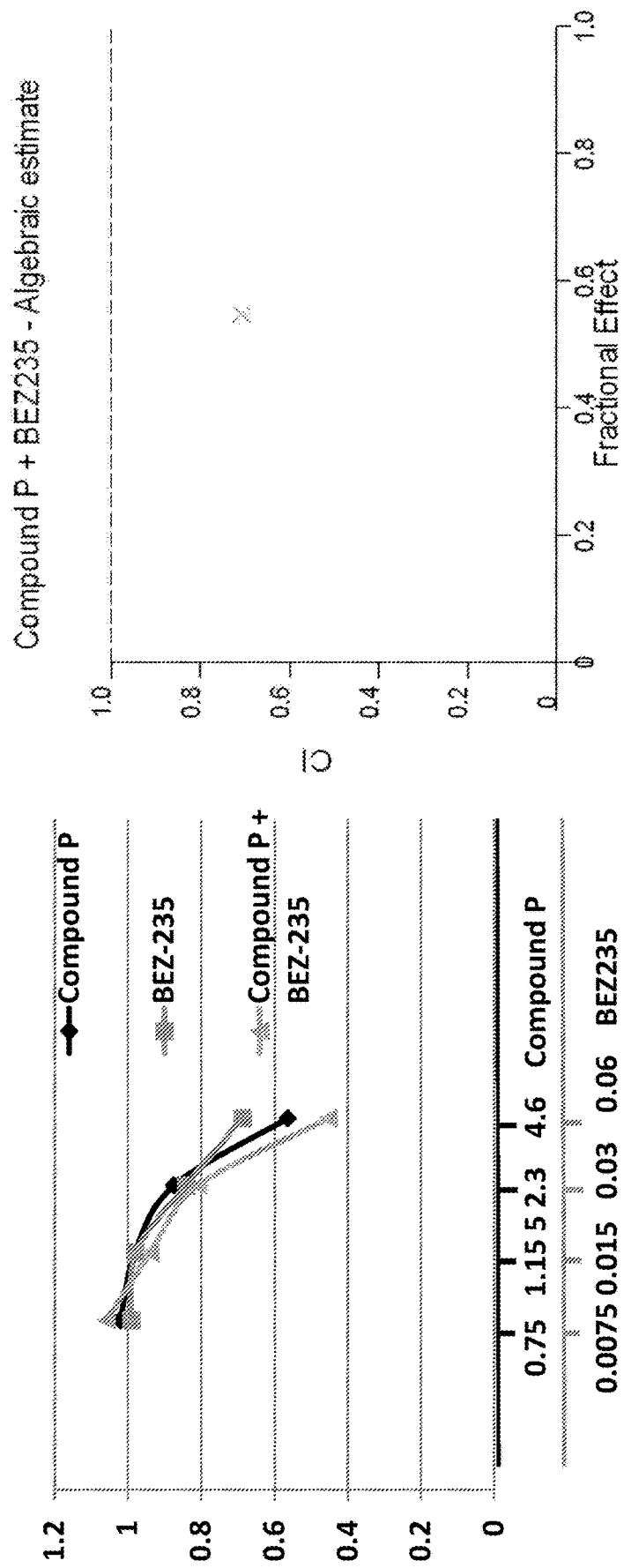
Figure 19:
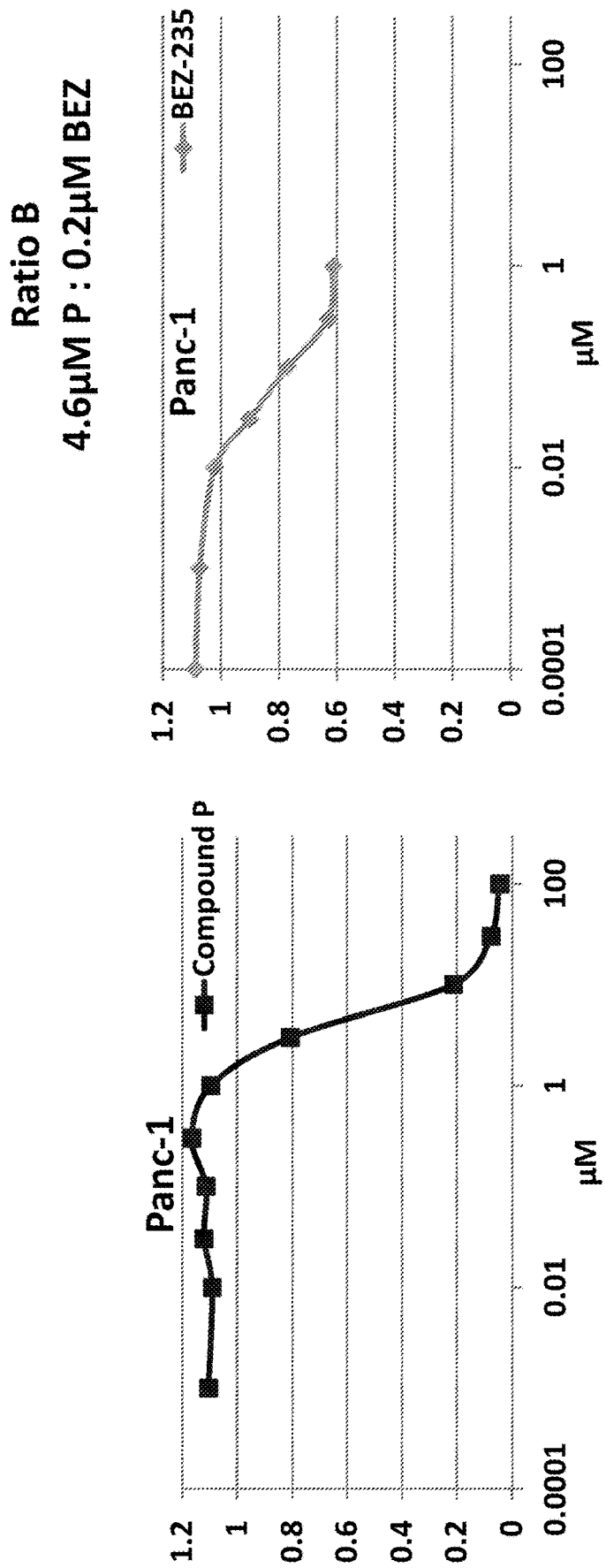
FIG. 19: Compound P+BEZ-235 Panc-1.
Figure 19:
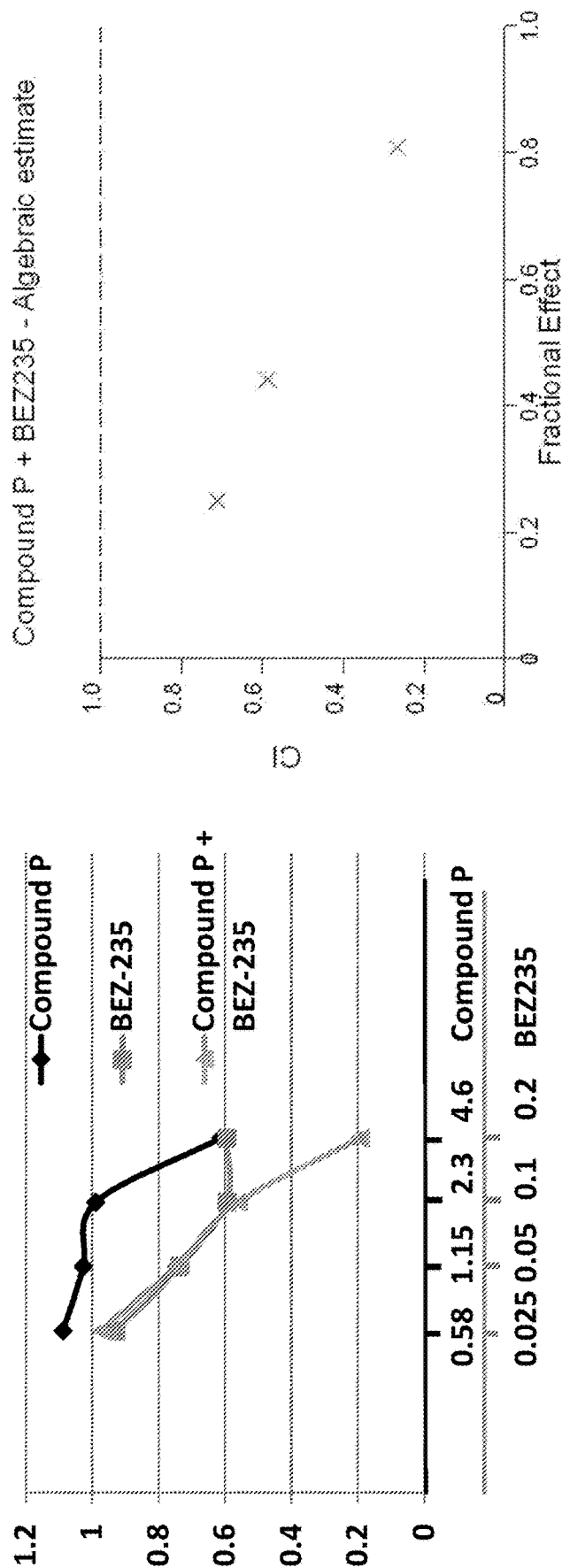
Figure 20:
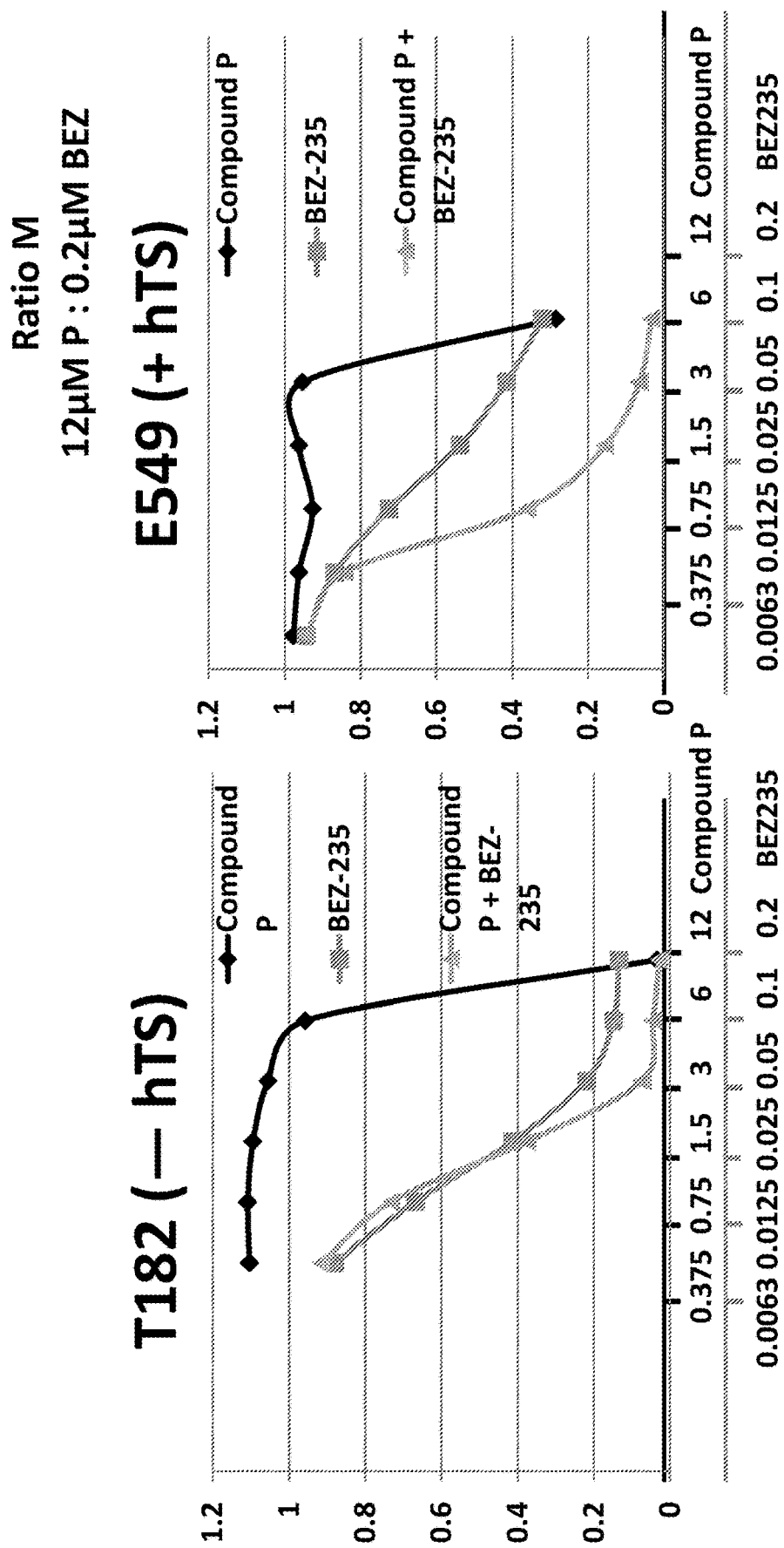
FIG. 20: Compound P+BEZ235 (Dual PI-3K/mTOR Inhibitor) in Pancreatic Ductal Adenocarcinoma Cell Lines Derived from KRAS/PTEN Mutant Mouse Tumors.

Table 1 provides a list of exemplary 4-quinolinemethanols that can be used in the formulation of compositions disclosed herein. Compound P, as used throughout this application, is mefloquine or a pharmaceutically acceptable salt thereof.

Table 2 provides a list of exemplary PI-3K inhibitors that can be used in the formulation of compositions disclosed herein.

Table 3 provides a list of exemplary AKT inhibitors that can be used in the formulation of compositions disclosed herein.

Table 4 provides a list of exemplary mTOR inhibitors that can be used in the formulation of compositions disclosed herein.

DETAILED DISCLOSURE OF THE INVENTION

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangably.

The following abbreviations and terms have the indicated meanings throughout: PI3K=Phosphoinositide-3-kinase; AKT=serine-threonine protein kinase B; mTOR=Mammalian target of rapamycin).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients where the terms "about" or "approximately" are used, these compositions contain the stated amount of the ingredient with a variation (error range) of 0-10% around the value (X±10%).

When ranges are used herein, such as for dose ranges, combinations and subcombinations of ranges (e.g., subranges within the disclosed range), specific embodiments therein are intended to be explicitly included.

"Treatment", "treating", "palliating" and "ameliorating" (and grammatical variants of these terms), as used herein, are used interchangeably. These terms refer to an approach for obtaining beneficial or desired results including but not limited to therapeutic benefit. A therapeutic benefit is achieved with the eradication or amelioration of one or more of the physiological symptoms associated with the underlying disorder such that an improvement is observed in the patient, notwithstanding that the patient may still be afflicted with the underlying disorder.

As used herein, the term "cancer" refers to the presence of cells possessing abnormal growth characteristics, such as uncontrolled proliferation, immortality, metastatic potential, rapid growth and proliferation rate, perturbed oncogenic signaling, and certain characteristic morphological features. This includes but is not limited to the growth of: (1) benign or malignant cells (e.g., tumor cells) that correlates with overexpression of a serine/threonine kinase; or (2) benign or malignant cells (e.g., tumor cells) that correlates with abnormally high levels of serine/threonine kinase activity or lipid kinase activity. Non-limiting serine/threonine kinases implicated in cancer include but are not limited to PI-3K mTOR, and AKT. Exemplary lipid kinases include but are not limited to PI3 kinases such as PBKα, PBKβ, PBKδ, and PBKγ.

The term "effective amount" or "therapeutically effective amount" refers to that amount of an inhibitor described herein that is sufficient to effect the intended application including but not limited to disease treatment. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

A "sub-therapeutic amount" of an agent is an amount less than the effective amount for that agent, but which when combined with an effective or sub-therapeutic amount of another agent or therapy can produce a desired result, due to, for example, synergy in the resulting efficacious effects (e.g., therapeutic benefit) for the patient, or reduced side effects associated with the compounds administered to the patient. Typical therapeutic amounts for an agent, as disclosed herein, can be ascertained from various publicly available sources (e.g., drugs.com, The Physician's Desk Reference, or scientific literature). Subtherapeutic amounts of an agent, as provided herein, are amounts less than those reported in the publicly available sources.

In the case of mefloquine, the therapeutic dose is 1000 mg per day. Thus, subtherapeutic doses of mefloquine (per day) are less than 1000 mg and can range from 5 mg to 950 mg, about 5 mg to about 500 mg, about 100 mg to about 500 mg, or about 200 to about 700 mg. For quinine, the therapeutic dose is 648 mg per day. Thus, subtherapeutic doses of quinine (per day) are less than range from 5 mg to 625 mg, about 5 mg to about 500 mg, about 100 mg to about 575 mg, or about 200 to about 500 mg. For idelalisib (CS-101), subtherapeutic doses (per day) are less than 300 mg. Thus, subtherapeutic doses can range from 5 mg to 250 mg, about 5 mg to about 150 mg, about 100 mg to about 125 mg, or about 50 to about 150 mg. For miltefosine, subtherapeutic doses (per day) are less than 150 mg per day for subjects of 45 kg or more or less than 100 mg per day for subjects between 30 and 44 kg. Thus, for subjects weighing more than 45 kg, subtherapeutic doses can range from 5 mg to 125 mg, about 5 mg to about 100 mg, about 100 mg to about 125 mg, or about 25 to about 125 mg. For sirolimus, subtherapeutic doses (per day) are less than 2 mg per day for subjects of 40 kg or more or less than 1 mg/m$^2$ (body surface area) per day for subjects less than 40 kg. Thus, for subjects weighing more than 40 kg, subtherapeutic doses (per day) can range from 0.1 mg to 1.95 mg, about 0.5 mg to about 1.75 mg, about 1 mg to about 1.50 mg, or about 0.25 to about 1.50 mg. For subjects weighing less than 40 kg, subtherapeutic doses (per day) can range from 0.1 mg to 0.95 mg, about 0.5 mg to about 0.75 mg, about 0.01 mg to about 0.75 mg, or about 0.25 to about 0.75 mg. For everolimus, subtherapeutic doses (per day) are less than 10 mg per day. Thus, subtherapeutic doses (per day) can range from 0.1 mg to 9.50 mg, about 0.5 mg to about 9.00 mg, about 1 mg to about 7.5 mg, or about 2.50 to about 5.0 mg. For temsirolimus, subtherapeutic doses are about 25 mg/week. Thus, subtherapeutic doses (per week) can range from 1 mg to 24.5 mg, about 0.5 mg to about 22 mg, about 1 mg to about 15 mg, or about 2.50 to about 20 mg.

A "synergistically effective" therapeutic amount or "synergistically effective" amount of an agent is an amount which, when combined with an effective or subtherapeutic amount of another agent or therapy, produces a greater effect than when either of the two agents are used alone. A synergistically effective therapeutic amount of an agent produces a greater effect when used in combination than the additive effects of each of the two agents or therapies when used alone. The term "greater effect" encompasses not only a reduction in symptoms of the disorder to be treated, but also an improved side effect profile, improved tolerability, improved patient compliance, improved efficacy, or any other improved clinical outcome.

As used herein, "agent" or "agents" refers to an inhibitor of PI3K, AKT and/or mTOR and one or more 4-quinolinemethanols. Exemplary agents are provided in Tables 1-4 of this application.

The terms "antagonist" and "inhibitor" may be used interchangeably, and they refer to a compound having the ability to inhibit a biological function of a target protein, whether by inhibiting the activity or expression of the target protein. Accordingly, the terms "antagonist" and "inhibitor" are defined in the context of the biological role of the target protein. Exemplary "antagonists" and "inhibitors" are provided in Tables 1-4 of this application.

The terms "co-administration," "administered in combination with," and their grammatical equivalents encompass administration of two or more agents to a subject so that both agents and/or their metabolites are present in the subject at the same time. Co-administration includes simultaneous administration in separate compositions, administration at different times in separate compositions, or administration in a composition in which both agents are present. Co-administered agents may be in the same formulation. Coadministered agents may also be in different formulations.

A "therapeutic effect," as used herein, encompasses a therapeutic benefit as described above. This includes delaying the appearance of a disease or condition, delaying the onset of symptoms of a disease or condition, slowing, halting, or reversing the progression of a disease or condition, or any combination thereof.

The term "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

"Subject" refers to an animal, such as a mammal, for example a human. The methods described herein can be useful in both pre-clinical human therapeutics and veterinary applications. In some embodiments, the subject is a mammal (such as an animal model of disease), and in some embodiments, the subject is human. The terms "subject" and "patient" can be used interchangably.

The terms "simultaneous" or "simultaneously" as applied to administering agents to a subject refer to administering one or more agents at the same time, or at two different time points that are separated by no more than 1 hour. The term "sequentially" refers to administering more than one agent at two different time points that are separated by more than 1 hour, e.g., about 2 hours, about 5 hours, 8 hours, 1 day, 2 days, 3 days, 4 days, 5 days, 6 days, 7 days or even longer.

The subject application provides methods of treating cancer comprising the administration or co-administration of a composition comprising one or more 4-quinolinemethanols and: a) one or more agents that inhibit the activity of Phosphoinositide-3-kinase (PI-3K); b) one or more agents that inhibit the activity of serine-threonine protein kinase B (AKT); c) one or more agents that inhibit the activity of mammalian target of rapamycin (mTOR); or d) any combination of one or more agents that inhibit the activity of PI-3K, AKT and mTOR. In certain embodiments, the 4-quinolinemethanol is selected from Table 1, the PI-3K inhibitor is selected from Table 2, the AKT inhibitor is selected from Table 3 and the mTOR inhibitor is selected from Table 4. In various embodiments, one or more 4-quinolinemethanols and one or more PI-3K inhibitors are administered simultaneously or sequentially. Other embodiments provide for the one or more 4-quinolinemethanols and one or more PI-3K inhibitors to be co-administered as a single composition. Yet other embodiments provide for one or more 4-quinolinemethanols and one or more AKT inhibitors to co-administered or administered simultaneously or sequentially. Yet another embodiment provides for one or more 4-quinolinemethanols and one or more AKT inhibitors to be co-administered as a single composition. Similarly, the disclosed method can comprise the administration or co-administration of more 4-quinolinemethanols and one or more mTOR inhibitors. As discussed herein, one or more 4-quinolinemethanols and one or more AKT inhibitors can be administered simultaneously or sequentially or as a single composition.

In various embodiments, subtherapeutic amounts of one or more 4-quinolinemethanols (4QM) and: a) one or more agents that inhibit the activity of Phosphoinositide-3-kinase (PI-3K); b) one or more agents that inhibit the activity of serine-threonine protein kinase B (AKT); c) one or more agents that inhibit the activity of mammalian target of rapamycin (mTOR); or d) any combination of one or more agents that inhibit the activity of PI-3K, AKT and mTOR can be administered or co-administered. The subtherapeutic amounts of these agents are preferably provided in synergistically effective amounts. Alternatively, the agents can be administered in subtherapeutic amounts in the following ratios:

one or more 4-quinolinemethanols (4QM) and one or more PI-3K inhibitors at a ratio (4QM:PI-K3I) of between 600:1 and 17.5:1;

one or more 4-quinolinemethanols (4QM) and one or more AKT inhibitors (AKTI) at a ratio (4QM:AKTI) of between 0.33:1 and 3:1;

one or more 4-quinolinemethanols (4QM) and one or more mTOR inhibitors (mTORI) at a ratio (4QM:mTORI) of between 1000:1 and 17.5:1; or various ratios falling within the ranges provided herein.

Cancers suitable for treatment according to the disclosed methods include, but are not limited to: Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-related cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone cancer, Bone tumor, Brain stem lioma, Brain tumor, Breast cancer, Brenner tumor, Bronchial tumor, Bronchioloalveolar carcinoma, Brown tumor, Burkitt's lymphoma, Cancer of unknown primary site, Carcinoid Tumor, Carcinoma, Carcinoma in situ, Carcinoma of the penis, Carcinoma of unknown primary site, Carcinosarcoma, Castleman's Disease, Central nervous system embryonal tumor, Cerebellar astrocytoma, Cerebral astrocytoma, Cervical cancer, Cholangiocarcinoma, Chondroma, Chondrosarcoma, Chordoma, Choriocarcinoma, Choroid plexus papilloma, Chronic lymphocytic leukemia, Chronic monocytic leukemia, Chronic myelogenous leukemia, Chronic myeloproliferative disorder, Chronic neutrophilic leukemia, Clear-cell tumor, Colon cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial uterine cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing family of tumor, Ewing family sarcoma, Ewing's sarcoma, Extracranial germ cell tumor, Extragonadal germ cell tumor, Extrahepatic bile duct cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric cancer, Gastric lymphoma, Gastrointestinal cancer, Gastrointestinal carcinoid tumor, Gastrointestinal stromal tumor, Gastrointestinal stromal tumor, Germ cell tumor, Germinoma, Gestational choriocarcinoma, Gestational trophoblastic tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin's lymphoma, Hypopharyngeal cancer, Hypothalamic glioma, Inflammatory breast cancer, Intraocular melanoma, Islet cell carcinoma, Islet cell tumor, Juvenile myelomonocytic leukemia, Sarcoma, Kaposi's sarcoma, Kidney cancer, Klatskin tumor, Krukenberg tumor, Laryngeal cancer, Lentigo maligna melanoma, Leukemia, Leukemia, Lip and oral cavity cancer, Liposarcoma, Lung cancer, Luteoma, Lymphangioma, Lymphangiosarcoma, Lymphoepithelioma, Lymphoid leukemia, Lymphoma, Macroglobulinemia, Malignant fibrous histiocytoma, Malignant fibrous histiocytoma of bone, Malignant glioma, Malignant mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloepithelioma, Melanoma, Melanoma, Meningioma, Merkel Cell Carcinoma, Mesothelioma, Metastatic squamous neck cancer with occult primary, Metastatic urothelial carcinoma, Mixed mullerian tumor, Monocytic leukemia, Mouth cancer, Mucinous tumor, Multiple endocrine neoplasia syndrome, Multiple myeloma, Mycosis fungoides, Myelodysplasia disease, Myelodysplasia syndromes, Myeloid leukemia, Myeloid sarcoma, Myeloproliferative disease, Myxoma, nasal cavity cancer, Nasopharyngeal cancer, Nasopharyngeal carcinoma, Neoplasm, Neurinoma, Neuroblastoma, Neuroblastoma, Neurofibroma, Neuroma, Nodular melanoma, Non-Hodgkin's lymphoma, Nonmelanoma skin cancer, Non-small cell lung cancer, Ocular oncology, Oligoastrocytoma, Oligodendroglioma, Oncocytoma, Optic nerve sheath meningioma, Oral cancer, Oropharyngeal cancer, Osteosarcoma, Osteosarcoma, Ovarian cancer, Ovarian epithelial cancer, Ovarian germ cell tumor, Ovarian low malignant potential tumor, Paget's disease of the breast, Pancoast tumor, Pancreatic cancer, Papillary thyroid cancer, Papillomatosis, Paraganglioma, Paranasal sinus cancer, Parathyroid cancer, Penile cancer, Perivascular epithelioid cell tumor, Pharyngeal cancer, Pheochromocytoma, Pineal parenchymal tumor of intermediate differentiation, Pineoblastoma, Pituicytoma, Pituitary adenoma, Pituitary tumor, Plasma cell neoplasm, Pleuropulmonary blastoma, Polyembryoma, precursor T-lymphoblastic lymphoma, Primary central nervous system lymphoma, Primary effusion lymphoma, Primary hepatocellular cancer, Primary liver cancer, Primary peritoneal cancer, Primitive neuroectodermal tumor, Prostate cancer, Pseudomyxoma peritonei, Rectal cancer, Renal cell carcinoma, Respiratory tract carcinoma involving the NUT gene on chromosome 15, Retinoblastoma, Rhabdomyoma, Rhabdomyosarcoma, Richter's transformation, Sacrococcygeal teratoma, Salivary gland cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin cancer, Small blue round cell tumor, Small cell carcinoma, Small cell lung cancer, Small cell lymphoma, Small intestine cancer, Soft tissue sarcoma, Somatostatinoma, Soot wart, Spinal cord tumor, Spinal tumor, Splenic marginal zone lymphoma, Squamous cell carcinoma, Stomach cancer, Superficial spreading melanoma, Supratentorial primitive neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat cancer, Thymic carcinoma, Thymoma, Thyroid cancer, Transitional Cell Cancer of renal pelvis and ureter, Transitional cell carcinoma, Urachal cancer, Urethral cancer, Urogenital neoplasm, Uterine sarcoma, Uveal melanoma, Vaginal cancer, Verner-Morrison syndrome, Verrucous carcinoma, Visual pathway glioma, Vulvar cancer, Waldenstrom's macroglobulinemia, Warthin's tumor, Wilms' tumor, or any combinations thereof.

In some embodiments, the cancer selected from the group consisting of non-small cell lung cancer, small cell lung cancer, head and neck squamous cell carcinoma, pancreatic cancer, breast cancer, ovarian cancer, renal cell carcinoma, prostate cancer, neuroendocrine cancer, gastric cancer, bladder cancer, a brain cancer (glioma, astrocytoma, glioblastoma multiforme, etc.), colon cancer and endometrial cancer.

The subject application also provides compositions comprising one or more 4-quinolinemethanols (4QM) and: a) one or more agents that inhibit the activity of Phosphoinositide-3-kinase (PI-3K); b) one or more agents that inhibit the activity of serine-threonine protein kinase B (AKT); c) one or more agents that inhibit the activity of mammalian target of rapamycin (mTOR); or d) any combination of one or more agents that inhibit the activity of PI-3K, AKT and mTOR. In various embodiments, subtherapeutic amounts of 4Qm and the other agents are provided within the composition. Some embodiments provide compositons containing subtherapeutic amounts of the agents disclosed herein in the following ratios:

one or more 4-quinolinemethanols (4QM) and one or more PI-3K inhibitors at a ratio (4QM:PI-K3I) of between 600:1 and 17.5:1;

one or more 4-quinolinemethanols (4QM) and one or more AKT inhibitors (AKTI) at a ratio (4QM:AKTI) of between 0.33:1 and 3:1;

one or more 4-quinolinemethanols (4QM) and one or more mTOR inhibitors (mTORT) at a ratio (4QM:mTORI) of between 1000:1 and 17.5:1; or various ratios falling within the ranges provided herein.

Other embodiments provide compositions comprising 4QM and various agents in subtherapeutic amounts. For example, subtherapeutic doses of mefloquine (per day) are less than 1000 mg and can range from 5 mg to 950 mg, about 5 mg to about 500 mg, about 100 mg to about 500 mg, or about 200 to about 700 mg. For quinine, the therapeutic dose is 648 mg per day. Thus, subtherapeutic doses of quinine (per day) can range from 5 mg to 625 mg, about 5 mg to about 500 mg, about 100 mg to about 575 mg, or about 200 to about 500 mg. For idelalisib (CS-101), subtherapeutic doses (per day) are less than 300 mg. Thus, subtherapeutic doses can range from 5 mg to 250 mg, about 5 mg to about 150 mg, about 100 mg to about 125 mg, or about 50 to about 150 mg. For miltefosine, subtherapeutic doses (per day) are less than 150 mg per day for subjects of 45 kg or more or less than 100 mg per day for subjects between 30 and 44 kg. Thus, for subjects weighing more than 45 kg, subtherapeutic doses can range from 5 mg to 125 mg, about 5 mg to about 100 mg, about 100 mg to about 125 mg, or about 25 to about 125 mg. For sirolimus, subtherapeutic doses (per day) are less than 2 mg per day for subjects of 40 kg or more or less than 1 mg/m$^2$ (body surface area) per day for subjects less than 40 kg. Thus, for subjects weighing more than 40 kg, subtherapeutic doses (per day) can range from 0.1 mg to 1.95 mg, about 0.5 mg to about 1.75 mg, about 1 mg to about 1.50 mg, or about 0.25 to about 1.50 mg. For subjects weighing less than 40 kg, subtherapeutic doses (per day) can range from 0.1 mg to 0.95 mg, about 0.5 mg to about 0.75 mg, about 0.01 mg to about 0.75 mg, or about 0.25 to about 0.75 mg. For everolimus, subtherapeutic doses (per day) are less than 10 mg per day. Thus, subtherapeutic doses (per day) can range from 0.1 mg to 9.50 mg, about 0.5 mg to about 9.00 mg, about 1 mg to about 7.5 mg, or about 2.50 to about 5.0 mg. For temsirolimus, subtherapeutic doses are about 25 mg/week. Thus, subtherapeutic doses (per week) can range from 1 mg to 24.5 mg, about 0.5 mg to about 22 mg, about 1 mg to about 15 mg, or about 2.50 to about 20 mg. In some embodiments, compositons containing subtherapeutic amounts of the other agents disclosed in Tables 1-4 can be readily asceratained from the literature and correspond to amounts that are between 5% and 95%, between 5% and 90%, between 5% and 80% or between 5% and 75% of the amounts reported to be therapeutically effective for any compound identified in Tables 1-4.

Other embodiments provide for a composition comprising one or more 4-quinolinemethanols (4QM) and: a) one or more agents that inhibit the activity of Phosphoinositide-3-kinase (PI-3K); b) one or more agents that inhibit the activity of serine-threonine protein kinase B (AKT); c) one or more agents that inhibit the activity of mammalian target of rapamycin (mTOR); or d) any combination of one or more agents that inhibit the activity of PI-3K, AKT and mTOR. Subtherapeutic amounts of these components of the composition correspond to amounts that are between 5% and 95%, between 5% and 90%, between 5% and 80% or between 5% and 75% of the amounts reported to be therapeutically effective for a given 4-quinolinemethanol (4QM) agent that inhibits the activity of Phosphoinositide-3-kinase (PI-3K), an agent that inhibits the activity of serine-threonine protein kinase B (AKT), or an agent that inhibit the activity of mammalian target of rapamycin (mTOR).

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1

Figure 22:
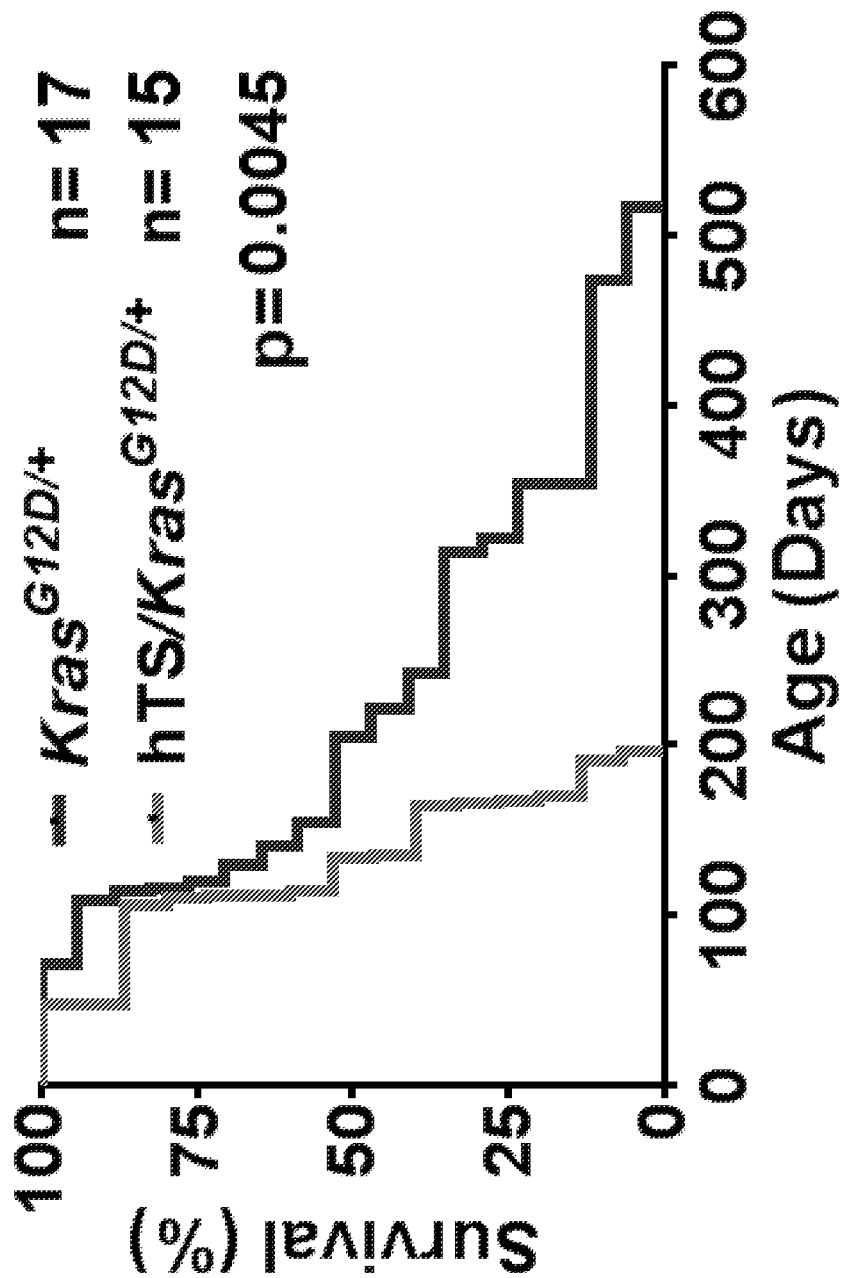
FIG. 22: TS Accelerates KRAS mutant PDAC.

In the present study, we show that human TS (hTS) significantly accelerates PDAC progression and metastases and decreases overall survival of Pdx1-Cre/LSL-Kras$^{G12D/+}$ mice (Kras$^{G12D/+}$ mice) and that dual targeting of TS and the Ras/PI-3K/AKT/mTOR pathway results in synergistic growth inhibition of PDAC in vitro and in vivo. Specifically, we demonstrate that a widely-used anti-parasitic agent (referred to as Compound P or mefloquine), which inhibits the enzymatic activity of human TS in a partial mixed-type manner, synergizes with inhibitors of the KRAS/PI-3K/AKT/mTOR pathway to inhibit PDAC in vitro and in vivo. In summary, we demonstrate that the oncogenes KRAS and TS cooperate to accelerate the progression of PDAC, and propose that combination therapies targeting these two oncogenic pathways should be evaluated in PDAC patients (see FIG. 22). Because our data demonstrate that Thymidylate Synthase and mutant Kras oncogenically cooperate to promote pancreatic cancer progression and metastasis, we next investigated whether targeting of either of these two oncogenic signals could inhibit pancreatic cancer growth in KRAS mutant cells. To accomplish this, we evaluated the effect of a novel partial mixed-type inhibitor of TS, compound P (mefloquine), or several KRAS effector inhibitors on the viability of 4 KRAS mutant PDAC cell lines (two human PDAC cell lines, MIA PaCa-2 and Panc-1, and two murine cell lines: T182, derived from a KrasG12D/+/Pten−/+ murine PDAC, and E549, derived from a hTS/KrasG12D/+/Pten−/+ mouse murine PDAC).

We treated each cell line with the mTOR inhibitor Everolimus, the AKT inhibitor MK-2206, the dual PI-3K/mTOR inhibitor BEZ235, and the MEK inhibitor Selumetinib, or Compound P (mefloquine), prior to viability assessment at 72 hours via MTT assay. We found that while the novel TS inhibitor Compound P was cytotoxic in all cell lines tested, the KRAS effector inhibitors varied in their growth inhibition effects: the mTOR inhibitor Everolimus was potently cytostatic, while the AKT inhibitor MK-2206 and the dual PI-3K/mTOR inhibitor BEZ235 were both fully cytotoxic in 3 out of 4 cell lines. However, none of the KRAS effector inhibitors were fully cytotoxic in Panc-1 cells. We found that the MEK inhibitor Selumetinib had little effect in the 4 PDAC cell lines (data not shown).

To determine optimal doses for combination, we first analyzed the viability dose-response curves for each drug. For the TS allosteric inhibitor (Compound P) we chose 12 μM as the optimal dose for combination in all cell lines, in order to capture the steep slope observed in the viability dose-response curve. For everolimus, we chose 0.1 μM as the optimal dose for combination in all cell lines, because the dose-response effect appeared to be cytostatic across 5 orders of magnitude (from 0.001 μM to 10 μM) and 0.1 μM is the midpoint order of magnitude in this range. For MK-2206, and BEZ-235, we chose doses which would capture the cytotoxicity of the dose-response viability curves: 8.0 μM for MK-2206, and 0.2 μM for BEZ235. The optimal dose for each drug was then serially diluted by one-half from the chosen optimal dose to $\frac{1}{32}$nd of the chosen optimal dose, such that six combination points could be analyzed. Because the ratio of each drug in each experiment remained constant in all serial dilutions, we refer to this method as the "fixed molar ratio method".

To determine the effect of combination treatment on cell viability, we treated the 4 PDAC cell lines with the TS inhibitor compound P combined with each of the KRAS effector inhibitors using the fixed molar ratio method, and analyzed individual drug curves and combination points using CalcuSyn software to assess for synergy. We found that simultaneous targeting of TS (by partial mixed-type inhibition of the homodimeric enzyme) and oncogenic KRAS (via targeting of the KRAS/PI3K/AKT/mTOR effector pathway) results in synergistic antitumor activity which is greater than that observed with either drug alone. Specifically, we found that the novel TS inhibitor Compound P synergized with the mTOR inhibitor Everolimus, the dual PI3K/mTOR inhibitor BEZ235, and the AKT inhibitor MK-2206 in four KRAS mutant pancreatic cancer cell lines when combined in a constant ratio method. Interestingly, synergy was not observed with the combination of the TS inhibitor compound P and the MEK inhibitor Selumetinib (data not shown).

TABLE 1

| List of Exemplary 4-Quinolinemethanols | |
|---|---|
| WR-142490 (Compound P; mefloquine) | [2,8-bis(trifluoromethyl)quinolin-4-yl]-piperidin-2-ylmethanol |
| Quinine | (R)-[(2S,4S,5R)-5-ethenyl-1-azabicyclo[2.2.2]octan-2-yl]-(6-methoxyquinolin-4-yl)methanol |
| Qunidine | (S)-[(2R,4S,5R)-5-ethenyl-1-azabicyclo[2.2.2]octan-2-yl]-(6-methoxyquinolin-4-yl)methanol |
| SN-10275 | (6,8-dichloro-2-phenylquinolin-4-yl)-piperidin-2-ylmethanol |
| WR-30090 | 2-(dibutylamino)-1-[6,8-dichloro-2-(3,4-dichlorophenyl)quinolin-4-yl]ethanol |
| WR-176990 | 1-[2,8-bis(trifluoromethyl)quinolin-4-yl]-2-(dibutylamino)ethanol |
| WR-177000 | 1-[2,8-bis(trifluoromethyl)quinolin-4-yl]-2-(butylamino)ethanol |
| WR-177973 | Identified in Table 1 of US 2011/0092488. |
| WR-183544 | 1-[2,8-Bis(trifluoromethyl)-4-quinolinyl]-2-(propylamino)ethanol |
| WR-183545 | 1-[2,8-Bis(trifluoromethyl)-4-quinolinyl]-2-(methylamino)ethanol |
| WR-184806 | 1-[2,8-bis(trifluoromethyl)quinolin-4-yl]-3-(tert-butylamino)propan-1-ol |
| WR-194965 | 4-tert-butyl-2-[(tert-butylamino)methyl]-6-(4-chlorophenyl)phenol |
| WR-211679 | Identified in Table 1 of US 2011/0092488. |
| WR-211925 | Identified in Table 1 of US 2011/0092488. |
| WR-226253 | (S)-[6,8-dichloro-2-(trifluoromethyl)quinolin-4-yl]-[(2S)-piperidin-2-yl]methanol; methanesulfonic acid |
| WR-308245 | 1-[2,8-bis(trifluoromethyl)quinolin-4-yl]-2-(methylamino)ethanol |
| WR-308246 | 1-[2,8-bis(trifluoromethyl)quinolin-4-yl]-2-(dimethylamino)ethanol |
| WR-308247 | 1-[2,8-bis(trifluoromethyl)quinolin-4-yl]-2-(2-fluoroethylamino)ethanol |
| WR-308251 | 2-anilino-1-[2,8-bis(trifluoromethyl)quinolin-4-yl]ethanol |
| WR-308252 | 2-(benzylamino)-1-[2,8-bis(trifluoromethyl)quinolin-4-yl]ethanol |
| WR-308253 | 1-[2,8-bis(trifluoromethyl)quinolin-4-yl]-2-(2-phenylethylamino)ethanol |
| WR-308254 | 1-[2,8-bis(trifluoromethyl)quinolin-4-yl]-2-(diethylamino)ethanol |
| WR-308257 | 1-[2,8-bis(trifluoromethyl)quinolin-4-yl]-2-(propan-2-ylamino)ethanol |
| WR-308258 | 1-[2,8-bis(trifluoromethyl)quinolin-4-yl]-2-(2-hydroxyethylamino)ethanol |
| WR-308277 | 1-[2,8-bis(trifluoromethyl)quinolin-4-yl]-2-(dipropylamino)ethanol |
| WR-308278 | 1-[2,8-bis(trifluoromethyl)quinolin-4-yl]-2-(3-methylsulfanylpropylamino)ethanol |
| WR-308314 | 2-amino-1-[2,8-bis(trifluoromethyl)quinolin-4-yl]ethanol |

TABLE 1-continued

| List of Exemplary 4-Quinolinemethanols | |
|---|---|
| WR-308396 | 2-[2-(benzylamino)ethylamino]-1-[2,8-bis(trifluoromethyl)quinolin-4-yl]ethanol |
| WR-308411 | 1-[2,8-bis(trifluoromethyl)quinolin-4-yl]-2-(2,2,2-trifluoroethylamino)ethanol |
| WR-308412 | 1-[2,8-bis(trifluoromethyl)quinolin-4-yl]-2-(2-methoxyethylamino)ethanol |
| WR-308413 | 1-[2,8-bis(trifluoromethyl)quinolin-4-yl]-2-(4-methylpentan-2-ylamino)ethanol |
| WR-308437 | 1-[2,8-bis(trifluoromethyl)quinolin-4-yl]-2-(2-ethyl-4-methylimidazol-1-yl)ethanol |
| WR-308442 | 1-[2,8-bis(trifluoromethyl)quinolin-4-yl]-2-(hexylamino)ethanol |
| WR-308446 | 1-[2,8-bis(trifluoromethyl)quinolin-4-yl]-2-[(4,6,6-trimethyl-3-bicyclo[3.1.1]heptanyl)amino]ethanol |
| WR-308607 | 1-[2,8-bis(trifluoromethyl)quinolin-4-yl]-2-(2-methylpropylamino)ethanol |
| WR-308621 | [2,8-bis(trifluoromethyl)quinolin-4-yl]-[[(2R)-pyrrolidin-2-yl]methylamino]methanol |
| WR-308622 | 1-[2,8-bis(trifluoromethyl)quinolin-4-yl]-2-(3-methoxypropylamino)ethanol |
| WR-308623 | 1-[2,8-bis(trifluoromethyl)quinolin-4-yl]-2-(2-propylimidazol-1-yl)ethanol |
| WR-308626 | 1-[2,8-bis(trifluoromethyl)quinolin-4-yl]-2-(2-propan-2-ylimidazol-1-yl)ethanol |
| WR-308632 | 1-[2,8-bis(trifluoromethyl)quinolin-4-yl]-2-butylsulfanylethanol |
| WR-308633 | 1-[2,8-bis(trifluoromethyl)quinolin-4-yl]-2-butoxyethanol |
| WR-308653 | 1-[2,8-bis(trifluoromethyl)quinolin-4-yl]heptan-1-ol |
| WR-308763 | 1-[2,8-bis(trifluoromethyl)quinolin-4-yl]-2-(2-methylbenzimidazol-1-yl)ethanol |
| WR-308764 | 2-(benzimidazol-1-yl)-1-[2,8-bis(trifluoromethyl)quinolin-4-yl]ethanol |
| WR-319535 | [[(1S,4R)-2-azabicyclo[2.2.1]heptan-4-yl]methylamino]-[2,8-bis(trifluoromethyl)quinolin-4-yl]methanol |
| WR-319581 | 2-[[(1R,4S)-2-azabicyclo[2.2.1]heptan-4-yl]methylamino]-1-[2,8-bis(trifluoromethyl)quinolin-4-yl]ethanol |

TABLE 2

| Exemplary PI-3K Inhibitors | |
|---|---|
| GDC-0941 | 4-[2-(1H-indazol-4-yl)-6-[(4-methylsulfonylpiperazin-1-yl)methyl]thieno[3,2-d]pyrimidin-4-yl]morpholine |
| NVP-BKM120 | 5-(2,6-dimorpholin-4-ylpyrimidin-4-yl)-4-(trifluoromethyl)pyridin-2-amine |
| PX-866 | [(3aR,6E,9S,9aR,10R,11aS)-6-[[bis(prop-2-enyl)amino]methylidene]-5-hydroxy-9-(methoxymethyl)-9a,11a-dimethyl-1,4,7-trioxo-2,3,3a,9,10,11-hexahydroindeno[4,5-h]isochromen-10-yl]acetate |
| GDC-0032 | 2-methyl-2-[4-[2-(5-methyl-2-propan-2-yl-1,2,4-triazol-3-yl)-5,6-dihydroimidazo[1,2-d][1,4]benzoxazepin-9-yl]pyrazol-1-yl]propanamide |
| GSK2636771 | 2-methyl-1-[[2-methyl-3-(trifluoromethyl)phenyl]methyl]-6-morpholin-4-ylbenzimidazole-4-carboxylic acid |
| IPI-145 | 8-chloro-2-phenyl-3-[(1S)-1-(7H-purin-6-ylamino)ethyl]isoquinolin-1-one |
| CAL-101 (GS-1101) | 5-fluoro-3-phenyl-2-[(1S)-1-(7H-purin-6-ylamino)propyl]quinazolin-4-one |
| LY294002 | 2-morpholin-4-yl-8-phenylchromen-4-one |
| Wortmannin | (1S,6bR,9aS,11R,11bR)-9a,11b-dimethyl-1-[(methyloxy)methyl]-3,6,9-trioxo-1,6,6b,7,8,9,9a,10,11,11b-decahydro-3H-furo[4,3,2-de]indeno[4,5-h]isochromen-11-yl acetate |
| Demethoxy-viridin | (1R,11bR)-1-Hydroxy-11b-methyl-1,7,8,11b-tetrahydrocyclopenta[7,8]phenanthro[10,1-bc]furan-3,6,9(2H)-trione |
| XL-147 | 2-amino-N-[3-[[3-(2-chloro-5-methoxyanilino)quinoxalin-2-yl]sulfamoyl]phenyl]-2-methylpropanamide |
| BAY80-6946 | 2-amino-N-[7-methoxy-8-(3-morpholin-4-ylpropoxy)-2,3-dihydroimidazo[1,2-c]quinazolin-5-yl]pyrimidine-5-carboxamide |
| ZSTK474 | 4-[4-[2-(difluoromethyl)benzimidazol-1-yl]-6-morpholin-4-yl-1,3,5-triazin-2-yl]morpholine |

TABLE 2-continued

Exemplary PI-3K Inhibitors

| | |
|---|---|
| BYL719 | (2S)-1-N-[4-methyl-5-[2-(1,1,1-trifluoro-2-methylpropan-2-yl)pyridin-4-yl]-1,3-thiazol-2-yl]pyrrolidine-1,2-dicarboxamide |
| MLN01117 (INK-1117) | |
| SAR260301 | (S)-2-(2-(2-methylindolin-1-yl)-2-oxoethyl)-6-morpholinopyrimidin-4(3H)-one |
| AMG319 | (S)-N-(1-(7-Fluoro-2-(pyridin-2-yl)quinolin-3-yl)ethyl)-9H-purin-6-amine |
| TGR-1202 (RP6530) | 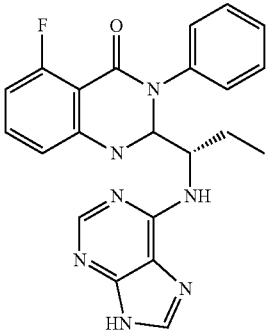 [SMILES: CC[C@H](Nc1ncnc2[nH]cnc12)C1Nc2cccc(F)c2C(=O)N1c1ccccc1] |
| IC87114 | 2-[(6-aminopurin-9-yl)methyl]-5-methyl-3-(2-methylphenyl)quinazolin-4-one |
| TG-100-115 | 3-[2,4-diamino-7-(3-hydroxyphenyl)pteridin-6-yl]phenol |
| CUDC-907 | N-hydroxy-2-[[2-(6-methoxypyridin-3-yl)-4-morpholin-4-ylthieno[3,2-d]pyrimidin-6-yl]methyl-methylamino]pyrimidine-5-carboxamide |
| AEZS-136 | |
| NVP-BAG956 | 2-methyl-2-[4-[2-methyl-8-(2-pyridin-3-ylethynyl)imidazo[4,5-c]quinolin-1-yl]phenyl]propanenitrile |
| PIK-75 | N-[(E)-(6-bromoimidazo[1,2-a]pyridin-3-yl)methylideneamino]-N,2-dimethyl-5-nitrobenzenesulfonamide; hydrochloride |
| PIK-90 | N-(7,8-dimethoxy-2,3-dihydroimidazo[1,2-c]quinazolin-5-yl)pyridine-3-carboxamide |
| TGX-221 | 9-(1-anilinoethyl)-7-methyl-2-morpholin-4-ylpyrido[1,2-a]pyrimidin-4-one |
| A5-252424 | 5-[5-(4-fluoro-2-hydroxy-phenyl)-furan-2-ylmethylene]-thiazolidine-2,4-dione |
| D-106669 | 1-ethyl-3-[3-(4-methylanilino)pyrido[2,3-b]pyrazin-6-yl]urea |
| A-66 | (2S)-N1-[2-(1,1-Dimethylethyl)-4'-methyl[4,5'-bithiazol]-2'-yl]-1,2-pyrrolidinedicarboxamide |
| BN108 | The solution containing 0.5 mg/mL of dried extract of *Anemarrhena asphodeloides* Bunge is also referred to herein as BN108. Active ingredient in BN108 is Timosaponin A3 |
| Timosaponin A3 | (2S,3R,4S,5S,6R)-2-{[(2R,3R,4S,5R,6R)-4,5-dihydroxy-6-(hydroxymethyl)-2-[(1'R,2'S,3R,4'S,7'S,8'R,9'S,12'S,13'S,16'S,18'R)-6,7',9',13'-tetramethyl-5'-oxaspiro[oxane-3,6'-pentacyclo[10.8.0.0$^{2,9}$.0$^{4,8}$.0$^{13,18}$]icosane]oxy]oxan-3-yl]oxy]-6-(hydroxymethyl)oxane-3,4,5-triol |

TABLE 3

Exemplary AKT inhibitors

| | |
|---|---|
| MK-2206 | 8-[4-(1-aminocyclobutyl)phenyl]-9-phenyl-2H-[1,2,4]triazolo[3,4-f][1,6]naphthyridin-3-one; dihydrochloride |
| Triciribine | (2R,3R,4S,5R)-2-(3-amino-5-methyl-1,4,5,6,8-pentaazaacenaphthylen-1(5H)-yl)-5-(hydroxymethyl)tetrahydrofuran-3,4-diol. |
| Triciribine-Phosphate | 1-(5-O-Phosphono-β-D-ribofuranosyl)-5-methyl-1,5-dihydro-1,4,5,6,8-pentaazaacenaphthylene-3-amine; 1,4,5,6,8-Pentaazaacenaphthylene-3-amino-1,5-dihydro-5-methyl-1-beta-D-ribofuranosyl 5'-monophosphate |
| Miltefosine | 2-(hexadecoxy-oxido-phosphoryl)oxyethyl-trimethyl-azanium |
| Perifosine (KRX-0401) | (1,1-dimethylpiperidin-1-ium-4-yl) octadecyl phosphate |
| RX-0201 | This is an antisense oligonucleotide having the following sequence:<br>5' gctgcatgatctccttggcg 3' |
| Erucylphosphocholine | [(Z)-docos-13-enyl] 2-(trimethylazaniumyl)ethyl phosphate |
| PBI-05204 | [(3S,5R,8R,9S,10S,13R,14S,16S,17R)-14-hydroxy-3-[(2R,4S,5S,6S)-5-hydroxy-4-methoxy-6-methyloxan-2-yl]oxy-10,13-dimethyl-17-(5-oxo-2H-furan-3-yl)-1,2,3,4,5,6,7,8,9,11,12,15,16,17-tetradecahydrocyclopenta[a]phenanthren-16-yl] acetate |
| GSK690693 | 4-[2-(4-amino-1,2,5-oxadiazol-3-yl)-1-ethyl-7-[[(3S)-piperidin-3-yl]methoxy]imidazo[4,5-c]pyridin-4-yl]-2-methylbut-3-yn-2-ol |
| XL-418 | 1-[3-[4-(3-bromo-2H-pyrazolo[3,4-d]pyrimidin-4-yl)piperazin-1-yl]-4-methyl-5-(2-pyrrolidin-1-ylethylamino)phenyl]-4,4,4-trifluorobutan-1-one |
| GDC-0068 | (2S)-2-(4-chlorophenyl)-1-[4-[(5R,7R)-7-hydroxy-5-methyl-6,7-dihydro-5H-cyclopenta[d]pyrimidin-4-yl]piperazin-1-yl]-3-(propan-2-ylamino)propan-1-one |
| GSK2110183 | N-[(2S)-1-amino-3-(3,4-difluorophenyl)propan-2-yl]-5-chloro-4-(4-chloro-2-methylpyrazol-3-yl)thiophene-2-carboxamide |
| GSK2141795 | N-[(2S)-1-amino-3-(3,4-difluorophenyl)propan-2-yl]-5-chloro-4-(4-chloro-2-methylpyrazol-3-yl)furan-2-carboxamide |
| ARQ-092 | |
| AZD5363 | (S)-4-amino-N-(1-(4-chlorophenyl)-3-hydroxypropyl)-1-(7H-pyrrolo[2,3-d]pyrimidin-4-yl)piperidine-4-carboxamide |

TABLE 4

| mTOR Inhibitors | |
|---|---|
| Sirolimus (Rapamycin) | (1R,9S,12S,15R,16E,18R,19R,21R,23S,24E,26E,28E,30S,32S,35R)-1,18-dihydroxy-12-[(2S)-1-[(1S,3R,4R)-4-hydroxy-3-methoxycyclohexyl]propan-2-yl]-19,30-dimethoxy-15,17,21,23,29,35-hexamethyl-11,36-dioxa-4-azatricyclo[30.3.1.0$^{4,9}$]hexatriaconta-16,24,26,28-tetraene-2,3,10,14,20-pentone |
| Everolimus | (1S,9R,15R,16E,18R,19R,21S,23S,24E,26E,28E,30S,32R,35S)-1,18-dihydroxy-12-[(2S)-1-[(1S,3R,4R)-4-(2-hydroxyethoxy)-3-methoxycyclohexyl]propan-2-yl]-19,30-dimethoxy-15,17,21,23,29,35-hexamethyl-11,36-dioxa-4-azatricyclo[30.3.1.0$^{4,9}$]hexatriaconta-16,24,26,28-tetraene-2,3,10,14,20-pentone |
| Tacrolimus | (1R,9S,12S,13R,14S,17R,18E,21S,23S,24R,25S,27R)-1,14-dihydroxy-12-[(1E)-1-[(1R,3R,4R)-4-hydroxy-3-methoxycyclohexyl]prop-1-en-2-yl]-23,25-dimethoxy-13,19,21,27-tetramethyl-17-(prop-2-en-1-yl)-11,28-dioxa-4-azatricyclo[22.3.1.0$^{4,9}$]octacos-18-ene-2,3,10,16-tetrone |
| Temsirolimus | (1R,2R,4S)-4-[(2R)-2-[(1R,9S,12S,15R,16E,18R,19R,21R,23S,24E,26E,28E,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$]hexatriaconta-16,24,26,28-tetraen-12-yl]propyl]-2-methoxycyclohexyl 3-hydroxy-2-(hydroxymethyl)-2-methylpropanoate |
| Deforolimus or Ridaforolimus | (1R,2R,4S)-4-[(2R)-2-[(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$]hexatriaconta-16,24,26,28-tetraen-12-yl]propyl]-2-methoxycyclohexyl dimethylphosphinate |
| AZD2014 | 3-[2,4-bis[(3S)-3-methylmorpholin-4-yl]pyrido[2,3-d]pyrimidin-7-yl]-N-methylbenzamide |
| MLN-0128 (INK-128) | 5-(4-amino-1-propan-2-ylpyrazolo[3,4-d]pyrimidin-3-yl)-1,3-benzoxazol-2-amine |
| CC-223 | 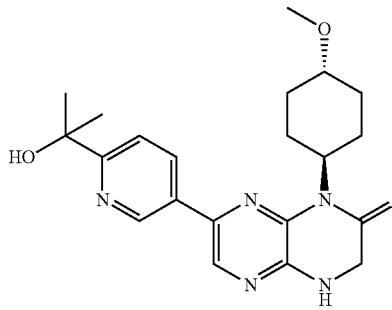 |
| Palomid 529 | 8-(1-hydroxyethyl)-2-methoxy-3-((4-methoxybenzyl)oxy)-6H-benzo[c]chromen-6-one |
| KU-0063794 | [5-[2-[(2R,6S)-2,6-dimethylmorpholin-4-yl]-4-morpholin-4-ylpyrido[2,3-d]pyrimidin-7-yl]-2-methoxyphenyl]methanol |
| Torin-1 | 1-[4-(4-propanoylpiperazin-1-yl)-3-(trifluoromethyl)phenyl]-9-quinolin-3-ylbenzo[h][1,6]naphthyridin-2-one |
| Torin-2 | 9-(6-aminopyridin-3-yl)-1-[3-(trifluoromethyl)phenyl]benzo[h][1,6]naphthyridin-2-one |
| DUAL PI-3K/mTOR Inhibitors | |
| NVP-BEZ235 | 2-methyl-2-[4-(3-methyl-2-oxo-8-quinolin-3-ylimidazo[4,5-c]quinolin-1-yl)phenyl]propanenitrile |
| NVP-BBD130 | 2-methyl-2-(4-(3-methyl-2-oxo-8-(2-(pyridin-3-yl)ethynyl)-2,3-dihydroimidazo[4,5-c]quinolin-1-yl)phenyl)propanenitrile |
| NVP-BGT226 | (Z)-but-2-enedioic acid;8-(6-methoxypyridin-3-yl)-3-methyl-1-[4-piperazin-1-yl-3-(trifluoromethyl)phenyl]imidazo[4,5-c]quinolin-2-one |
| LY3023414 | Identified in US20140377258 without providing structure or IUPAC name. |
| GDC-0890 | |
| PF-05212384 (PKI-587) | 1-[4-[4-(dimethylamino)piperidine-1-carbonyl]phenyl]-3-[4-(4,6-dimorpholin-4-yl-1,3,5-triazin-2-yl)phenyl]urea |

TABLE 4-continued

| | |
|---|---|
| XL-765 | N-[4-[[3-(3,5-dimethoxyanilino)quinoxalin-2-yl]sulfamoyl]phenyl]-3-methoxy-4-methylbenzamide |
| GSK2126458 | 2,4-difluoro-N-[2-methoxy-5-(4-pyridazin-4-ylquinolin-6-yl)pyridin-3-yl]benzenesulfonamide |
| PWT33597 (VCD-597) | |
| PI-103 | 3-(4-morpholin-4-ylpyrido[2,3]furo[2,4-b]pyrimidin-2-yl)phenol |
| GNE-477 | 5-[7-methyl-6-[(4-methylsulfonylpiperazin-1-yl)methyl]-4-morpholin-4-ylthieno[3,2-d]pyrimidin-2-yl]pyrimidin-2-amine |
| SF-1126 | L-Serine, N2-(1,4-dioxo-4-((4-(4-oxo-8-phenyl-4H-1-benzopyran-2-yl)morpholinium-4-yl)methoxy)butyl)-L-arginylglycyl-L-alpha-aspartyl-, inner salt |
| GSK1059615 | (5Z)-5-[(4-pyridin-4-ylquinolin-6-yl)methylidene]-1,3-thiazolidine-2,4-dione |
| PF-04691502 | 2-amino-8-[4-(2-hydroxyethoxy)cyclohexyl]-6-(6-methoxypyridin-3-yl)-4-methylpyrido[2,3-d]pyrimidin-7-one |

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

We claim:

1. A method of treating pancreatic cancer comprising the administration of a composition comprising one or more 4-quinolinemethanols and:

a) one or more Phosphoinositide-3-kinase (PI-3K) inhibitors;

b) one or more serinethreonine protein kinase B (AKT) inhibitors;

c) one or more mammalian target of rapamycin (mTOR) inhibitors; or d) any combination of one or more PI-3K inhibitors, AKT inhibitors, and mTOR inhibitors.

2. The method according to claim 1, wherein said 4-quinolinemethanol is selected from the group consisting of:

| Compound | Chemical name |
|---|---|
| WR-142490 (Compound P; mefloquine) | [2,8-bis(trifluoromethyl)quinolin-4-yl]-piperidin-2-ylmethanol, |
| Quinine | (R)-[(2S,4S,5R)-5-ethenyl-1-azabicyclo[2.2.2]octan-2-yl]-(6-methoxyquinolin-4-yl)methanol, |
| Qunidine | (S)-[(2R,4S,5R)-5-ethenyl-1-azabicyclo[2.2.2]octan-2-yl]-(6-methoxyquinolin-4-yl)methanol, |
| SN-10275 | (6,8-dichloro-2-phenylquinolin-4-yl)-piperidin-2-ylmethanol, |
| WR-30090 | 2-(dibutylamino)-1-[6,8-dichloro-2-(3,4-dichlorophenyl)quinolin-4-yl]ethanol, |
| WR-176990 | 1-[2,8-bis(trifluoromethyl)quinolin-4-yl]-2-(dibutylamino)ethanol, |
| WR-177000 | 1-[2,8-bis(trifluoromethyl)quinolin-4-yl]-2-(butylamino)ethanol, |

-continued

| Compound | Chemical name |
|---|---|
| WR-177973 | [structure shown with $R_{2a}$, $R_{2b}$, $R_{2c}$, $R_3$, $R_{4a}$, $R_{4b}$, $R_{4c}$, $R_6$, $R_7$, $R_8$ substituents on a quinoline-phenyl system with CH(OH)CH$_2$N linker] where $R_{2a}$ is t-Bu; $R_{2b}$, $R_{2c}$, $R_3$, $R_{4c}$, $R_7$, and $R_8$ are each hydrogen; $R_{4a}$ and $R_{4b}$ are each n-Bu; and $R_6$ is —Cl, |
| WR-183544 | 1-[2,8-Bis(trifluoromethyl)-4-quinolinyl]-2-(propylamino)ethanol, |
| WR-183545 | 1-[2,8-Bis(trifluoromethyl)-4-quinolinyl]-2-(methylamino)ethanol, |
| WR-184806 | 1-[2,8-bis(trifluoromethyl)quinolin-4-yl]-3-(tert-butylamino)propan-1-ol, |
| WR-194965 | 4-tert-butyl-2-[(tert-butylamino)methyl]-6-(4-chlorophenyl)phenol, |
| WR-211679 | [structure shown with $R_{2a}$, $R_{2b}$, $R_{2c}$, $R_3$, $R_{4a}$, $R_{4b}$, $R_{4c}$, $R_6$, $R_7$, $R_8$ substituents on a quinoline-phenyl system with CH(OH)CH$_2$N linker] where $R_{2a}$, $R_{2b}$, $R_{2c}$, $R_3$, $R_{4c}$, $R_6$, and $R_7$ are each hydrogen; $R_{4a}$ and $R_{4b}$ are each n-hexyl; and $R_8$ is —Cl, |

-continued

| Compound | Chemical name |
|---|---|
| WR-211925 | 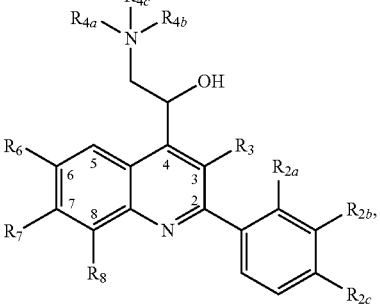 where $R_{2a}$, $R_{2b}$, $R_3$, $R_{4c}$, $R_6$, and $R_7$ are each hydrogen; $R_{4a}$ and $R_{4b}$ are each n-butyl; $R_{2c}$ is —Cl; and $R_8$ is —Me, |
| WR-226253 | (S)-[6,8-dichloro-2-(trifluoromethyl)quinolin-4-yl]-[(2S)-piperidin-2-yl]methanol; methanesulfonic acid, |
| WR-308245 | 1-[2,8-bis(trifluoromethyl)quinolin-4-yl]-2-(methylamino)ethanol, |
| WR-308246 | 1-[2,8-bis(trifluoromethyl)quinolin-4-yl]-2-(dimethylamino)ethanol, |
| WR-308247 | 1-[2,8-bis(trifluoromethyl)quinolin-4-yl]-2-(2-fluoroethylamino)ethanol, |
| WR-308251 | 2-anilino-1-[2,8-bis(trifluoromethyl)quinolin-4-yl]ethanol |
| WR-308252 | 2-(benzylamino)-1-[2,8-bis(trifluoromethyl)quinolin-4-yl]ethanol, |
| WR-308253 | 1-[2,8-bis(trifluoromethyl)quinolin-4-yl]-2-(2-phenylethylamino)ethanol, |
| WR-308254 | 1-[2,8-bis(trifluoromethyl)quinolin-4-yl]-2-(diethylamino)ethanol, |
| WR-308257 | 1-[2,8-bis(trifluoromethyl)quinolin-4-yl]-2-(propan-2-ylamino)ethanol, |
| WR-308258 | 1-[2,8-bis(trifluoromethyl)quinolin-4-yl]-2-(2-hydroxyethylamino)ethanol, |
| WR-308277 | 1-[2,8-bis(trifluoromethyl)quinolin-4-yl]-2-(dipropylamino)ethanol, |
| WR-308278 | 1-[2,8-bis(trifluoromethyl)quinolin-4-yl]-2-(3-methylsulfanylpropylamino)ethanol, |
| WR-308314 | 2-amino-1-[2,8-bis(trifluoromethyl)quinolin-4-yl]ethanol, |
| WR-308396 | 2-[2-(benzylamino)ethylamino]-1-[2,8-bis(trifluoromethyl)quinolin-4-yl]ethanol, |
| WR-308411 | 1-[2,8-bis(trifluoromethyl)quinolin-4-yl]-2-(2,2,2-trifluoroethylamino)ethanol, |
| WR-308412 | 1-[2,8-bis(trifluoromethyl)quinolin-4-yl]-2-(2-methoxyethylamino)ethanol, |
| WR-308413 | 1-[2,8-bis(trifluoromethyl)quinolin-4-yl]-2-(4-methylpentan-2-ylamino)ethanol, |
| WR-308437 | 1-[2,8-bis(trifluoromethyl)quinolin-4-yl]-2-(2-ethyl-4-methylimidazol-1-yl)ethanol, |
| WR-308442 | 1-[2,8-bis(trifluoromethyl)quinolin-4-yl]-2-(hexylamino)ethanol, |
| WR-308446 | 1-[2,8-bis(trifluoromethyl)quinolin-4-yl]-2-[(4,6,6-trimethyl-3-bicyclo[3.1.1]heptanyl)amino]ethanol, |
| WR-308607 | 1-[2,8-bis(trifluoromethyl)quinolin-4-yl]-2-(2-methylpropylamino)ethanol, |
| WR-308621 | [2,8-bis(trifluoromethyl)quinolin-4-yl]-[[(2R)-pyrrolidin-2-yl]methylamino]methanol, |
| WR-308622 | 1-[2,8-bis(trifluoromethyl)quinolin-4-yl]-2-(3-methoxypropylamino)ethanol, |
| WR-308623 | 1-[2,8-bis(trifluoromethyl)quinolin-4-yl]-2-(2-propylimidazol-1-yl)ethanol, |
| WR-308626 | 1-[2,8-bis(trifluoromethyl)quinolin-4-yl]-2-(2-propan-2-ylimidazol-1-yl)ethanol, |
| WR-308632 | 1-[2,8-bis(trifluoromethyl)quinolin-4-yl]-2-butylsulfanylethanol, |
| WR-308633 | 1-[2,8-bis(trifluoromethyl)quinolin-4-yl]-2-butoxyethanol, |
| WR-308653 | 1-[2,8-bis(trifluoromethyl)quinolin-4-yl]heptan-1-ol, |
| WR-308763 | 1-[2,8-bis(trifluoromethyl)quinolin-4-yl]-2-(2-methylbenzimidazol-1-yl)ethanol, |
| WR-308764 | 2-(benzimidazol-1-yl)-1-[2,8-bis(trifluoromethyl)quinolin-4-yl]ethanol, |
| WR-319535 | [[(1S,4R)-2-azabicyclo[2.2.1]heptan-4-yl]methylamino]-[2,8-bis(trifluoromethyl)quinolin-4-yl]methanol, and |
| WR-319581 | 2-[[(1R,4S)-2-azabicyclo[2.2.1]heptan-4-yl]methylamino]-1-[2,8-bis(trifluoromethyl)quinolin-4-yl]ethanol; | said PI-3K inhibitor is selected from the group consisting of:

| Compound | Chemical name |
|---|---|
| GDC-0941 | 4-[2-(1H-indazol-4-yl)-6-[(4-methylsulfonylpiperazin-1-yl)methyl]thieno[3,2-d]pyrimidin-4-yl]morpholine, |
| NVP-BKM120 | 5-(2,6-dimorpholin-4-ylpyrimidin-4-yl)-4-(trifluoromethyl)pyridin-2-amine, |
| PX-866 | [(3aR,6E,9S,9aR,10R,11aS)-6-[[bis(prop-2-enyl)amino]methylidene]-5-hydroxy-9-(methoxymethyl)-9a,11a-dimethyl-1,4,7-trioxo-2,3,3a,9,10,11-hexahydroindeno[4,5-h]isochromen-10-yl]acetate, |
| GDC-0032 | 2-methyl-2-[4-[2-(5-methyl-2-propan-2-yl-1,2,4-triazol-3-yl)-5,6-dihydroimidazo[1,2-d][1,4]benzoxazepin-9-yl]pyrazol-1-yl]propanamide, |
| GSK2636771 | 2-methyl-1-[[2-methyl-3-(trifluoromethyl)phenyl]methyl]-6-morpholin-4-ylbenzimidazole-4-carboxylic acid, |
| IPI-145 | 8-chloro-2-phenyl-3-[(1S)-1-(7H-purin-6-ylamino)ethyl]isoquinolin-1-one, |
| CAL-101 (GS-1101) | 5-fluoro-3-phenyl-2-[(1S)-1-(7H-purin-6-ylamino)propyl]quinazolin-4-one, |
| LY294002 | 2-morpholin-4-yl-8-phenylchromen-4-one, |
| Wortmannin | (1S,6bR,9aS,11R,11bR)-9a,11b-dimethyl-1-[(methyloxy)methyl]-3,6,9-trioxo-1,6,6b,7,8,9,9a,10,11,11b-decahydro-3H-furo[4,3,2-de]indeno[4,5-h]isochromen-11-yl acetate, |
| Demethoxy-viridin | (1R,11bR)-1-Hydroxy-11b-methyl-1,7,8,11b-tetrahydrocyclopenta[7,8]phenanthro[10,1-bc]furan-3,6,9(2H)-trione, |
| XL-147 | 2-amino-N-[3-[[3-(2-chloro-5-methoxyanilino)quinoxalin-2-yl]sulfamoyl]phenyl]-2-methylpropanamide, |
| BAY80-6946 | 2-amino-N-[7-methoxy-8-(3-morpholin-4-ylpropoxy)-2,3-dihydroimidazo[1,2-c]quinazolin-5-yl]pyrimidine-5-carboxamide, |

-continued

| Compound | Chemical name |
|---|---|
| ZSTK474 | 4-[4-[2-(difluoromethyl)benzimidazol-1-yl]-6-morpholin-4-yl-1,3,5-triazin-2-yl]morpholine, |
| BYL719 | (2S)-1-N-[4-methyl-5-[2-(1,1,1-trifluoro-2-methylpropan-2-yl)pyridin-4-yl]-1,3-thiazol-2-yl]pyrrolidine-1,2-dicarboxamide, |
| MLN01117 (INK-1117) | [6-(2-amino-1,3-benzoxazol-5-yl)imidazo[1,2-a]pyridin-3-yl]-morpholin-4-ylmethanone |
| SAR260301 | (S)-2-(2-(2-methylindolin-1-yl)-2-oxoethyl)-6-morpholinopyrimidin-4(3H)-one, |
| AMG319 | (S)-N-(1-(7-Fluoro-2-(pyridin-2-yl)quinolin-3-yl)ethyl)-9H-purin-6-amine, |
| TGR-1202 (RP6530) | [chemical structure] |
| IC87114 | 2-[(6-aminopurin-9-yl)methyl]-5-methyl-3-(2-methylphenyl)quinazolin-4-one, |
| TG-100-115 | 3-[2,4-diamino-7-(3-hydroxyphenyl)pteridin-6-yl]phenol, |
| CUDC-907 | N-hydroxy-2-[[2-(6-methoxypyridin-3-yl)-4-morpholin-4-ylthieno[3,2-d]pyrimidin-6-yl]methyl-methylamino]pyrimidine-5-carboxamide, |
| AEZS-136 | |
| NVP-BAG956 | 2-methyl-2-[4-[2-methyl-8-(2-pyridin-3-ylethynyl)imidazo[4,5-c]quinolin-1-yl]phenyl]propanenitrile, |
| PIK-75 | N-[(E)-(6-bromoimidazo[1,2-a]pyridin-3-yl)methylideneamino]-N,2-dimethyl-5-nitrobenzenesulfonamide; hydrochloride, |
| PIK-90 | N-(7,8-dimethoxy-2,3-dihydroimidazo[1,2-c]quinazolin-5-yl)pyridine-3-carboxamide, |
| TGX-221 | 9-(1-anilinoethyl)-7-methyl-2-morpholin-4-ylpyrido[1,2-a]pyrimidin-4-one, |
| A5-252424 | 5-[5-(4-fluoro-2-hydroxy-phenyl)-furan-2-ylmethylene]-thiazolidine-2,4-dione, |
| D-106669 | 1-ethyl-3-[3-(4-methylanilino)pyrido[2,3-b]pyrazin-6-yl]urea, |
| A-66 | (2S)-N1-[2-(1,1-Dimethylethyl)-4'-methyl[4,5'-bithiazol]-2'-yl]-1,2-pyrrolidinedicarboxamide, |
| BN108 | The solution containing 0.5 mg/mL of dried extract of *Anemarrhena asphodeloides* Bunge, with active ingredient of Timosaponin A3; and |
| Timosaponin A3 | (2S,3R,4S,5S,6R)-2-{[(2R,3R,4S,5R,6R)-4,5-dihydroxy-6-(hydroxymethyl)-2-[(1'R,2'S,3R,4'S,7'S,8'R,9'S,12'S,13'S,16'S,18'R)-6,7',9',13'-tetramethyl-5'-oxaspiro[oxane-3,6'-pentacyclo[10.8.0.0$^{2,9}$.0$^{4,8}$.0$^{13,18}$]icosane]oxy]oxan-3-yl]oxy}-6-(hydroxymethyl)oxane-3,4,5-triol; | said AKT inhibitor is selected from the group consisting of:

TABLE 3

| Compound | Chemical name |
|---|---|
| MK-2206 | 8-[4-(1-aminocyclobutyl)phenyl]-9-phenyl-2H-[1,2,4]triazolo[3,4-f][1,6]naphthyridin-3-one; dihydrochloride, |
| Triciribine | (2R,3R,4S,5R)-2-(3-amino-5-methyl-1,4,5,6,8-pentaazaacenaphthylen-1(5H)-yl)-5-(hydroxymethyl)tetrahydrofuran-3,4-diol, |
| Triciribine-Phosphate | 1-(5-O-Phosphono-β-D-ribofuranosyl)-5-methyl-1,5-dihydro-1,4,5,6,8-pentaazaacenaphthylene-3-amine; 1,4,5,6,8-Pentaazaacenaphthylene-3-amino-1,5-dihydro-5-methyl-1-beta-D-ribofuranosyl 5'-monophosphate |

TABLE 3-continued

| Compound | Chemical name |
|---|---|
| Miltefosine | 2-(hexadecoxy-oxido-phosphoryl)oxyethyl-trimethyl-azanium, |
| Perifosine (KRX-0401) | (1,1-dimethylpiperidin-1-ium-4-yl) octadecyl phosphate, |
| RX-0201 | 5' gctgcatgatctccttggcg 3', |
| Erucylphosphocholine | [(Z)-docos-13-enyl] 2-(trimethylazaniumyl)ethyl phosphate |
| PBI-05204 | [(3S,5R,8R,9S,10S,13R,14S,16S,17R)-14-hydroxy-3-[(2R,4S,5S,6S)-5-hydroxy-4-methoxy-6-methyloxan-2-yl]oxy-10,13-dimethyl-17-(5-oxo-2H-furan-3-yl)-1,2,3,4,5,6,7,8,9,11,12,15,16,17-tetradecahydrocyclopenta[a]phenanthren-16-yl] acetate, |
| GSK690693 | 4-[2-(4-amino-1,2,5-oxadiazol-3-yl)-1-ethyl-7-[[(3S)-piperidin-3-yl]methoxy]imidazo[4,5-c]pyridin-4-yl]-2-methylbut-3-yn-2-ol, |
| XL-418 | 1-[3-[4-(3-bromo-2H-pyrazolo[3,4-d]pyrimidin-4-yl)piperazin-1-yl]-4-methyl-5-(2-pyrrolidin-1-ylethylamino)phenyl]-4,4,4-trifluorobutan-1-one, |
| GDC-0068 | (2S)-2-(4-chlorophenyl)-1-[4-[(5R,7R)-7-hydroxy-5-methyl-6,7-dihydro-5H-cyclopenta[d]pyrimidin-4-yl]piperazin-1-yl]-3-(propan-2-ylamino)propan-1-one, |
| GSK2110183 | N-[(2S)-1-amino-3-(3,4-difluorophenyl)propan-2-yl]-5-chloro-4-(4-chloro-2-methylpyrazol-3-yl)thiophene-2-carboxamide, |
| GSK2141795 | N-[(2S)-1-amino-3-(3,4-difluorophenyl)propan-2-yl]-5-chloro-4-(4-chloro-2-methylpyrazol-3-yl)furan-2-carboxamide, |
| ARQ-092 | 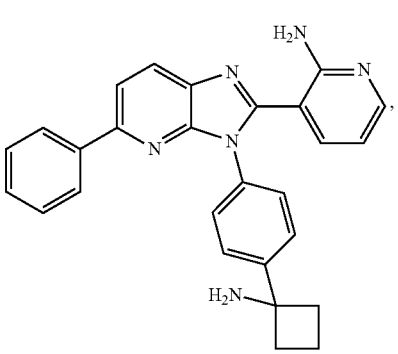 [SMILES: Nc1ncccc1-c1nc2ccc(-c3ccccc3)nc2n1-c1ccc(C2(N)CCC2)cc1] and |
| AZD5363 | (S)-4-amino-N-(1-(4-chlorophenyl)-3-hydroxypropyl)-1-(7H-pyrrolo[2,3-d]pyrimidin-4-yl)piperidine-4-carboxamide; | and said mTOR inhibitor is selected from the group consisting of:

| Compound | Chemical name |
|---|---|
| Sirolimus (Rapamycin) | (1R,9S,12S,15R,16E,18R,19R,21R,23S,24E,26E,28E,30S,32S,35R)-1,18-dihydroxy-12-[(2S)-1-[(1S,3R,4R)-4-hydroxy-3-methoxycyclohexyl]propan-2-yl]-19,30-dimethoxy-15,17,21,23,29,35-hexamethyl-11,36-dioxa-4-azatricyclo[30.3.1.0$^{4,9}$]hexatriaconta-16,24,26,28-tetraene-2,3,10,14,20-pentone, |
| Everolimus | (1S,9R,15R,16E,18R,19R,21S,23R,24E,26E,28E,30S,32R,35S)-1,18-dihydroxy-12-[(2S)-1-[(1S,3R,4R)-4-(2-hydroxyethoxy)-3-methoxycyclohexyl]propan-2-yl]-19,30-dimethoxy-15,17,21,23,29,35-hexamethyl-11,36-dioxa-4-azatricyclo[30.3.1.0$^{4,9}$]hexatriaconta-16,24,26,28-tetraene-2,3,10,14,20-pentone, |
| Tacrolimus | (1R,9S,12S,13R,14S,17R,18E,21S,23S,24R,25S,27R)-1,14-dihydroxy-12-[(1E)-1-[(1R,3R,4R)-4-hydroxy-3-methoxycyclohexyl]prop-1-en-2-yl]-23,25-dimethoxy-13,19,21,27-tetramethyl-17-(prop-2-en-1-yl)-11,28-dioxa-4-azatricyclo[22.3.1.0$^{4,9}$]octacos-18-ene-2,3,10,16-tetrone, |
| Temsirolimus | (1R,2R,4S)-4-[(2R)-2-[(1R,9S,12S,15R,16E,18R,19R,21R,23S,24E,26E,28E,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$]hexatriaconta-16,24,26,28-tetraen-12-yl]propyl]-2-methoxycyclohexyl 3-hydroxy-2-(hydroxymethyl)-2-methylpropanoate, |
| Deforolimus or Ridaforolimus | (1R,2R,4S)-4-[(2R)-2-[(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$]hexatriaconta-16,24,26,28-tetraen-12-yl]propyl]-2-methoxycyclohexyl dimethylphosphinate, |
| AZD2014 | 3-[2,4-bis[(3S)-3-methylmorpholin-4-yl]pyrido[2,3-d]pyrimidin-7-yl]-N-methylbenzamide; and |
| MLN-0128 (INK-128) | 5-(4-amino-1-propan-2-ylpyrazolo[3,4-d]pyrimidin-3-yl)-1,3-benzoxazol-2-amine. |

3. The method according to claim 1, wherein one or more 4-quinolinemethanols and one or more PI-3K inhibitors are co-administered.

4. The method according to claim 1, wherein one or more 4-quinolinemethanols and one or more AKT inhibitors are co-administered.

5. The method according to claim 1, wherein one or more 4-quinolinemethanols and one or more mTOR inhibitors are co-administered.

6. The method according to claim 1, wherein one or more 4-quinolinemethanols and one or more PI-3K inhibitors are administered at a ratio of between 600:1 and 17.5:1.

7. The method according to claim 1, wherein one or more 4-quinolinemethanols and one or more AKT inhibitors are administered at a ratio of between 0.33:1 and 3:1.

8. The method according to claim 1, wherein one or more 4-quinolinemethanols and one or more mTOR inhibitors are administered at a ratio of between 1000:1 and 17.5:1.

9. The method according to claim 1, said method comprising the co-administration of synergistically effective amounts of one or more 4-quinolinemethanols and:
   a) one or more Phosphoinositide-3-kinase (PI-3K) inhibitors;
   b) one or more serinethreonine protein kinase B (AKT) inhibitors;
   c) one or more mammalian target of rapamycin (mTOR) inhibitors; or
   d) any combination of one or more PI-3K inhibitors, AKT inhibitors, and mTOR inhibitors.

10. The method according to claim 9, wherein said synergistically effective amounts are subtherapeutic levels of one or more 4-quinolinemethanols; and
   a) one or more PI-3K inhibitors;
   b) one or more AKT inhibitors;
   c) one or more mTOR inhibitors; or
   d) any combination of one or more PI-3K inhibitors, AKT inhibitors, and mTOR inhibitors.

11. The method according to claim 1, wherein said one or more 4-quinolinemethanols and:
   a) one or more Phosphoinositide-3-kinase (PI-3K) inhibitors;
   b) one or more serine-threonine protein kinase B (AKT) inhibitors;
   c) one or more mammalian target of rapamycin (mTOR) inhibitors; or
   d) any combination of one or more PI-3K inhibitors, AKT inhibitors, and mTOR inhibitors;
   are compounds selected from Tables 1-4.

12. The method according to claim 11, wherein said composition comprises mefloquine and everolimus, mefloquine and MK-2206, or mefloquine and NVP-BEZ235.

13. The method of claim 1, wherein the 4-quinolinemethanol is mefloquine.

14. The method of claim 1, wherein the PI-3K inhibitor and the mTOR inhibitor is NVP-BEZ235.

15. The method of claim 1, wherein the AKT inhibitor is MK-2206.

16. The method of claim 1, wherein the mTOR inhibitor is everolimus.

17. The method according to claim 1, wherein one or more 4-quinolinemethanols and one or more PI-3K inhibitors are administered simultaneously.

18. The method according to claim 1, wherein one or more 4-quinolinemethanols and one or more PI-3K inhibitors are administered sequentially.

19. The method according to claim 1, wherein one or more 4-quinolinemethanols and one or more AKT inhibitors are administered simultaneously.

20. The method according to claim 1, wherein one or more 4-quinolinemethanols and one or more AKT inhibitors are administered sequentially.

21. The method of claim 1, wherein the 4-quinolinemethanol is mefloquine and the AKT inhibitor is MK-2206.

22. The method of claim 1, wherein the 4-quinolinemethanol is mefloquine and the mTOR inhibitor is everolimus.

23. The method of claim 1, wherein the 4-quinolinemethanol is mefloquine and the PI-3K inhibitor and the mTOR inhibitor is NVP-BEZ235.

24. The method according to claim 1, wherein one or more 4-quinolinemethanols and one or more mTOR inhibitors are co-administered.

25. The method of claim 1, wherein the pancreatic cancer is pancreatic ductal adenocarcinoma.

26. The method of claim 1, wherein the pancreatic cancer is islet cell carcinoma.

27. The method of claim 1, wherein the pancreatic cancer is squamous cell carcinoma.

28. The method of claim 1, wherein the pancreatic cancer is neuroendocrine cancer.

* * * * *

UNITED STATES PATENT AND TRADEMARK OFFICE
CERTIFICATE OF CORRECTION

PATENT NO.        : 10,835,524 B2
APPLICATION NO.   : 15/737545
DATED             : November 17, 2020
INVENTOR(S)       : Maria Zajac-Kaye et al.

It is certified that error appears in the above-identified patent and that said Letters Patent is hereby corrected as shown below:

In the Claims

In Claim 1, at Column 17, Lines 41-42, the text: "b) one or more serinethreonine protein kinase B (AKT) inhibitors" should be replaced with: --b) one or more serine-threonine protein kinase B (AKT) inhibitors--.

In Claim 2, at Column 21, the text: "The solution containing 0.5 mg/mL of dried extract of" should be replaced with: --Solution containing 0.5 mg/mL of dried extract of--.

In Claim 9, at Column 25, Lines 19-20, the text: "b) one or more serinethreonine protein kinase B (AKT) inhibitors" should be replaced with: --b) one or more serine-threonine protein kinase B (AKT) inhibitors--.

Signed and Sealed this
Second Day of November, 2021

Drew Hirshfeld
*Performing the Functions and Duties of the*
*Under Secretary of Commerce for Intellectual Property and*
*Director of the United States Patent and Trademark Office*